United States Patent
Solomon et al.

(10) Patent No.: US 10,166,339 B2
(45) Date of Patent: Jan. 1, 2019

(54) DISINFECTING CAP FOR MEDICAL CONNECTORS

(71) Applicant: Merit Medical Systems, Inc., South Jordan, UT (US)

(72) Inventors: Donald D. Solomon, North Salt Lake, UT (US); F. Mark Ferguson, Salt Lake City, UT (US); Mahender Avula, Salt Lake City, UT (US); Robert Hitchcock, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 400 days.

(21) Appl. No.: 14/947,341

(22) Filed: Nov. 20, 2015

(65) Prior Publication Data

US 2016/0144118 A1     May 26, 2016

Related U.S. Application Data

(60) Provisional application No. 62/083,817, filed on Nov. 24, 2014.

(51) Int. Cl.
    *B65D 81/24*      (2006.01)
    *A61M 5/30*      (2006.01)
    (Continued)

(52) U.S. Cl.
    CPC .............. *A61M 5/30* (2013.01); *A61M 5/002* (2013.01); *A61M 39/162* (2013.01); *A61M 39/20* (2013.01); *A61M 2005/3117* (2013.01)

(58) Field of Classification Search
    CPC .... A61M 39/162; A61M 39/165; A61M 5/30; A61M 5/002; A61M 39/20; A61M 2005/3117
(Continued)

(56) References Cited

U.S. PATENT DOCUMENTS

| 1,744,026 A | 10/1926 | Baltzley |
| 1,868,200 A | 7/1932 | Freedman |

(Continued)

FOREIGN PATENT DOCUMENTS

| CN | 205549223 | 9/2016 |
| EP | 0229786 | 7/1987 |

(Continued)

OTHER PUBLICATIONS

Office Action dated Feb. 27, 2018 for U.S. Appl. No. 14/978,925.
(Continued)

*Primary Examiner* — Luan K Bui
(74) *Attorney, Agent, or Firm* — Stoel Rives LLP

(57) ABSTRACT

A disinfecting cap accepts a needleless injection site to apply an antiseptic agent. The cap includes a breakable seal located in a chamber between the proximal and distal portions so as to be spaced away from the opening. The cap body may include a compliant wall that deforms when a needleless injection site is inserted into the opening to removably hold the cap on the needleless injection site. In lieu of a compliant wall, a flexible skirt may extend from the cap body into the proximal portion, so that when a needleless injection site is inserted into the opening, the flexible skirt engages the outer diameter of the needleless injection site to removably hold the cap on the needleless injection site. A carrier strip may be used, wherein each of the plurality of disinfecting caps is removably attached at its proximal end to the carrier strip.

8 Claims, 19 Drawing Sheets

(51) Int. Cl.
 *A61M 5/00* (2006.01)
 *A61M 39/16* (2006.01)
 *A61M 39/20* (2006.01)
 *A61M 5/31* (2006.01)

(58) Field of Classification Search
 USPC ......... 206/210, 820; 422/294, 300; 604/256,
 604/263, 533, 905
 See application file for complete search history.

(56) References Cited

U.S. PATENT DOCUMENTS

| | | |
|---|---|---|
| 2,356,969 A | 5/1942 | Blum |
| 2,299,037 A | 10/1942 | Saueressig |
| 2,351,804 A | 6/1944 | Blum |
| 3,315,830 A | 4/1967 | Flynn |
| 3,431,548 A | 3/1969 | Busler |
| 3,446,596 A | 5/1969 | Salivar et al. |
| 3,976,311 A | 8/1976 | Spendlove |
| 3,987,930 A | 10/1976 | Fuson |
| 4,121,727 A | 10/1978 | Robbins et al. |
| 4,232,677 A | 11/1980 | Leibinsohn |
| 4,324,239 A | 4/1982 | Gordon et al. |
| 4,334,551 A | 6/1982 | Pfister |
| 4,344,551 A | 6/1982 | Pfister |
| 4,340,052 A | 7/1982 | Dennehey et al. |
| 4,346,703 A | 8/1982 | Dennehey et al. |
| 4,354,490 A | 10/1982 | Rogers |
| 4,369,781 A | 1/1983 | Gilson et al. |
| 4,402,691 A | 9/1983 | Rosenthal et al. |
| 4,432,764 A | 2/1984 | Lopez |
| 4,432,766 A | 2/1984 | Bellotti et al. |
| 4,440,207 A | 4/1984 | Genatempo ............ A61L 31/16 150/154 |
| 4,450,624 A | 5/1984 | Collier |
| 4,572,373 A | 2/1986 | Johansson |
| 4,597,758 A | 7/1986 | Aalto et al. |
| 4,624,664 A | 11/1986 | Peluso ............... A61M 39/165 604/256 |
| 4,667,837 A | 5/1987 | Vitello et al. |
| 4,671,306 A | 6/1987 | Spector |
| 4,778,447 A | 10/1988 | Velde et al. |
| 4,798,303 A | 1/1989 | Arnold |
| 4,810,241 A | 3/1989 | Rogers |
| 4,838,875 A | 6/1989 | Somor |
| D303,631 S | 9/1989 | Demarest |
| D310,542 S | 9/1990 | Regnault |
| 4,991,629 A | 2/1991 | Ernesto et al. |
| 5,006,114 A | 4/1991 | Rogers et al. |
| 5,184,742 A | 2/1993 | Decaprio et al. |
| D333,788 S | 3/1993 | Geschwender |
| 5,190,534 A | 3/1993 | Kendell |
| 5,195,957 A | 3/1993 | Tollini |
| 5,205,821 A | 4/1993 | Kruger ............... A61M 39/162 604/535 |
| 5,242,425 A | 9/1993 | White et al. |
| D340,112 S | 10/1993 | Zeman |
| D341,227 S | 11/1993 | Lang et al. |
| 5,269,771 A | 12/1993 | Thomas et al. |
| 5,385,372 A | 1/1995 | Utterberg |
| 5,439,451 A | 8/1995 | Collinson et al. |
| 5,445,270 A | 8/1995 | Dratz |
| 5,451,113 A | 9/1995 | Lund et al. |
| 5,466,219 A | 11/1995 | Lynn et al. |
| 5,492,147 A | 2/1996 | Challender ............ F16L 29/005 137/614.05 |
| 5,536,258 A | 7/1996 | Folden |
| 5,554,135 A | 9/1996 | Menyhay |
| 5,694,978 A | 12/1997 | Heilmann et al. |
| 5,702,017 A | 12/1997 | Goncalves |
| 5,738,663 A | 4/1998 | Lopez |
| 5,792,120 A | 8/1998 | Menyhay |
| 5,894,015 A | 4/1999 | Rechtin |
| 5,951,519 A | 9/1999 | Utterberg |
| 5,954,657 A | 9/1999 | Rados |
| 5,954,957 A | 9/1999 | Chin-Loy et al. |
| 6,045,539 A | 4/2000 | Menyhay |
| 6,152,913 A | 11/2000 | Feith et al. |
| 6,171,287 B1 | 1/2001 | Lynn et al. |
| D456,668 S | 5/2002 | Tse |
| D468,015 S | 12/2002 | Horppu |
| D470,888 S | 2/2003 | Kuboshima |
| 6,523,686 B1 | 2/2003 | Bae |
| 6,932,795 B2 | 8/2005 | Lopez et al. |
| 6,960,191 B2 | 11/2005 | Howlett et al. |
| 7,014,169 B2 | 3/2006 | Newton et al. |
| 7,040,598 B2 | 5/2006 | Raybuck |
| 7,040,669 B2 | 5/2006 | Kenmotsu et al. |
| 7,198,611 B2 | 4/2007 | Connell et al. |
| D545,964 S | 7/2007 | Blanco |
| D547,446 S | 7/2007 | Racz et al. |
| D550,355 S | 9/2007 | Racz et al. |
| 7,282,186 B2 | 10/2007 | Lake, Jr. et al. |
| 7,316,669 B2 | 1/2008 | Ranalletta |
| D573,643 S | 7/2008 | Brigham et al. |
| D607,325 S | 1/2010 | Rogers et al. |
| 7,762,524 B2 | 7/2010 | Cawthon et al. |
| 7,762,988 B1 | 7/2010 | Vitello |
| 7,763,006 B2 | 7/2010 | Tennican |
| 7,780,794 B2 | 8/2010 | Rogers et al. .................... 134/6 |
| D632,574 S | 2/2011 | Huntington et al. |
| 7,922,701 B2 | 4/2011 | Buchman |
| D639,421 S | 6/2011 | Sano et al. |
| 7,985,302 B2 | 7/2011 | Rogers et al. ............ 134/115 R |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,231,602 B2 | 7/2012 | Anderson et al. |
| 8,273,303 B2 | 9/2012 | Ferlic et al. |
| 8,328,767 B2 | 12/2012 | Solomon et al. |
| 8,343,112 B2 | 1/2013 | Solomon et al. |
| 8,419,713 B1 | 4/2013 | Solomon et al. |
| 8,523,830 B2 | 9/2013 | Solomon et al. ............. 604/256 |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,740,864 B2 | 6/2014 | Hoang |
| 8,784,388 B2 | 7/2014 | Charles et al. |
| 8,808,637 B2 | 8/2014 | Ferlic |
| 8,961,475 B2 | 2/2015 | Solomon et al. |
| 9,079,692 B2 | 7/2015 | Solomon et al. |
| 9,101,750 B2 | 8/2015 | Solomon et al. |
| 9,114,915 B2 | 8/2015 | Solomon et al. |
| 9,242,084 B2 | 1/2016 | Solomon et al. |
| 9,352,140 B2 | 5/2016 | Kerr et al. |
| 2002/0093192 A1 | 7/2002 | Matkovich |
| 2003/0140441 A1 | 7/2003 | Stafford |
| 2003/0153865 A1 | 8/2003 | Connell et al. |
| 2003/0181849 A1 | 9/2003 | Castellanos |
| 2003/0198502 A1 | 10/2003 | Maloney et al. |
| 2004/0039341 A1 | 2/2004 | Ranalletta |
| 2004/0195136 A1 | 10/2004 | Young et al. |
| 2004/0201216 A1 | 10/2004 | Segal et al. |
| 2004/0214316 A1 | 10/2004 | O'Connell |
| 2004/0258560 A1 | 12/2004 | Lake, Jr. .................... A61L 2/18 422/28 |
| 2005/0033267 A1 | 2/2005 | Decaria |
| 2005/0038397 A1 | 2/2005 | Newton et al. |
| 2005/0124970 A1 | 6/2005 | Kunin et al. |
| 2005/0147524 A1 | 7/2005 | Bousquet |
| 2005/0183971 A1 | 8/2005 | Petricca |
| 2005/0203460 A1 | 9/2005 | Kim |
| 2005/0245883 A1 | 11/2005 | Baldwin |
| 2005/0265773 A1 | 12/2005 | De Laforcade .... A45D 40/0087 401/202 |
| 2005/0266714 A1 | 12/2005 | Higgins et al. |
| 2006/0030827 A1 | 2/2006 | Raulerson et al. |
| 2006/0177250 A1 | 8/2006 | Nakagaki |
| 2007/0112333 A1 | 5/2007 | Hoang et al. .................... 604/533 |
| 2007/0202177 A1 | 8/2007 | Hoang |
| 2007/0282280 A1 | 12/2007 | Tennican |

(56) References Cited

U.S. PATENT DOCUMENTS

| | | | |
|---|---|---|---|
| 2007/0287989 A1 | 12/2007 | Crawford et al. | |
| 2007/0293818 A1 | 12/2007 | Stout et al. | |
| 2007/0293822 A1 | 12/2007 | Crawford et al. | |
| 2008/0019889 A1 | 1/2008 | Rogers et al. | |
| 2008/0021381 A1 | 1/2008 | Lurvey et al. | |
| 2008/0027399 A1 | 1/2008 | Harding et al. | |
| 2008/0033371 A1 | 2/2008 | Updegraff | A61M 39/162 604/263 |
| 2008/0038167 A1 | 2/2008 | Lynn | |
| 2008/0039803 A1 | 2/2008 | Lynn | |
| 2008/0097407 A1 | 2/2008 | Plishka | |
| 2008/0086091 A1 | 4/2008 | Anderson et al. | |
| 2008/0095680 A1 | 4/2008 | Steffens et al. | |
| 2008/0105704 A1 | 5/2008 | Pritchard | |
| 2008/0107564 A1 | 5/2008 | Sternberg et al. | |
| 2008/0132880 A1 | 6/2008 | Buchman | |
| 2008/0147047 A1 | 6/2008 | Davis et al. | |
| 2008/0177250 A1 | 7/2008 | Howlett et al. | |
| 2008/0190485 A1 | 8/2008 | Guala | |
| 2008/0235888 A1 | 10/2008 | Vaillancourt et al. | |
| 2009/0008393 A1 | 1/2009 | Howlett et al. | |
| 2009/0062766 A1 | 3/2009 | Howlett et al. | |
| 2009/0099529 A1 | 4/2009 | Anderson et al. | |
| 2009/0149819 A1 | 6/2009 | Chelak | |
| 2009/0205151 A1 | 8/2009 | Fisher et al. | |
| 2010/0003067 A1 | 1/2010 | Shaw et al. | |
| 2010/0047123 A1 | 2/2010 | Solomon et al. | |
| 2010/0049170 A1 | 2/2010 | Solomon et al. | |
| 2010/0063482 A1 | 3/2010 | Mansour et al. | |
| 2010/0100056 A1 | 4/2010 | Cawthon et al. | |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | |
| 2011/0054440 A1 | 3/2011 | Lewis | |
| 2011/0064512 A1 | 3/2011 | Shaw et al. | |
| 2011/0165020 A1 | 7/2011 | Truggvason | |
| 2011/0213341 A1 | 9/2011 | Solomon et al. | |
| 2011/0217212 A1 | 9/2011 | Solomon et al. | |
| 2011/0232020 A1 | 9/2011 | Rogers et al. | |
| 2011/0277788 A1 | 11/2011 | Rogers et al. | |
| 2011/0314619 A1 | 12/2011 | Schweikert | |
| 2012/0016318 A1 | 1/2012 | Hoang et al. | |
| 2012/0039764 A1 | 2/2012 | Solomon | |
| 2012/0039765 A1 | 2/2012 | Solomon | |
| 2012/0216359 A1 | 8/2012 | Rogers | B08B 1/00 15/104.93 |
| 2013/0164189 A1 | 6/2013 | Hadden | A61M 39/16 422/300 |
| 2013/0171030 A1 | 7/2013 | Ferlic et al. | |
| 2013/0197485 A1 | 8/2013 | Gardner et al. | |
| 2014/0010481 A1 | 1/2014 | Last et al. | |
| 2014/0135739 A1 | 5/2014 | Solomon et al. | |
| 2015/0231384 A1 | 8/2015 | Ma | A61M 39/20 604/539 |
| 2015/0374968 A1 | 12/2015 | Solomon et al. | |
| 2016/0045629 A1 | 2/2016 | Gardner et al. | |
| 2016/0106968 A1 | 4/2016 | Solomon et al. | |

FOREIGN PATENT DOCUMENTS

| | | | |
|---|---|---|---|
| EP | 0462355 | 12/1991 | |
| JP | 64002760 | 1/1989 | |
| WO | 2004035245 | 4/2004 | |
| WO | 2006099306 A2 | 9/2006 | |
| WO | 2008089196 A2 | 7/2008 | |
| WO | 2008100950 A2 | 8/2008 | |
| WO | 2010002808 A1 | 1/2010 | |
| WO | 2010141508 A1 | 12/2010 | |
| WO | 2011141508 | 12/2010 | |
| WO | 2011053924 A1 | 5/2011 | |
| WO | 2011066565 A1 | 6/2011 | |
| WO | 2011066586 A1 | 6/2011 | |
| WO | WO 2015/174953 A1 | 11/2015 | A61L 2/16 |

OTHER PUBLICATIONS

Office Action dated Apr. 4, 2018 for U.S. Appl. No. 14/845,004.
Office Action dated Apr. 26, 2018 for U.S. Appl. No. 14/797,533.
Office Action dated Nov. 17, 2017 for U.S. Appl. No. 14/845,004.
Notice of Allowance dated Sep. 1, 2017 for U.S. Appl. No. 14/162,207.
Office Action dated Oct. 20, 2017 for U.S. Appl. No. 15/203,002.
European Search Report dated Mar. 6, 2012 for EP08727689.5.
European Search Report dated Jun. 20, 2017 for EP10827614.8.
International Search Report and Written Opinion dated Jan. 26, 2011 for PCT/US2010/058404.
International Search Report and Written Opinion dated Jan. 6, 2011 for PCT/US2010/054995.
International Search Report and Written Opinion dated Feb. 7, 2011 for PCT/US2010/058453.
International Search Report and Written Opinion dated Aug. 1, 2008 for PCT/US2008/051087.
International Search Report with Written Opinion dated Aug. 31, 2009 for PCT/US2009/049094.
Notice of Allowance dated Jun. 7, 2017 for U.S. Appl. No. 14/162,207.
Office Action dated Jan. 27, 2010 for U.S. Appl. No. 12/014,388.
Office Action dated Apr. 22, 2011 for U.S. Appl. No. 12/164,310.
Office Action dated May 5, 2009 for U.S. Appl. No. 12/014,388.
Office Action dated Jun. 9, 2011 for U.S. Appl. No. 12/171,997.
Office Action dated Jun. 21, 2010 for U.S. Appl. No. 12/014,388.
Office Action dated Aug. 16, 2010 for U.S. Appl. No. 12/164,310.
Office Action dated Dec. 23, 2010 for U.S. Appl. No. 12/014,388.
Baxa Corporation Launches PadLock Set Saver for IV Safety press release, 2 pages, available at http://www.pr.com/press-release/55432. ,Oct. 10, 2007.
Baxa Corporation Padlock catalog, 3 pages, copyright 2009, available at http://www.baxa.com/SearchResults/ProductDetail/?id=6452BFB9-3048-7B87-701697FB93902BA6.
Baxa Corporation Padlock Microbial Testing Technical Paper, copyright 2007, 4 pages, available at http://www.baxa.com/resources/docs/technicalPapers/PadLockMicrobialChallengeTechPaper.pdf.
Baxa Corporation PadLock Set Saver Specifications and Instructions for Use, copyright 2007, 2 pages, available at http://www.baxa.com/resources/docs/5300103905C.pdf.
BD Q-Syte Luer Access Split Septum product brochure, 4 pages, available at http://www.bd.com/infusion/pdfs/D16333.pdf. ,Nov. 2008.
Braun product catalog, 2pages. ,Aug. 2008.
Curos Port Protector, web page from http://www.iveramed.com/ ,Jul. 11, 2008.
Curos Port Protector product brochure, 2 pages, available at http://www.iveramed.com/clocs/Curos%20Brochure--FINAL.pdf. ,Nov. 2008.
Hospira Male/Female Sterile Cap product packaging insert and brochure, 2 pages. ,Aug. 2004.
Kippmed Vented Non-Vented Female Luer Lock Caps, The KippGroup, ,Jan. 1995 ,2 pgs.
Tego Connector product brochure, 2 pages, available at http://www.icumed.com/Docs-Tego/M1-1148%20TEG0%20Folder%20Brochure%20Rev.3.pdf. ,Nov. 2008.
Unomedical Medical Products catalog, 2 pages, available at http://www.unomedical.net/au/section05/section10/LocalSSI/..%5C..%5Cpdf%5Cmedical.pdf ,Jan. 2006.
Buchman, et al.,A New Central Venous Catheter Cap: Decreased Microbial Growth and Risk for Catheter-Related Bloodstream Infection, The Journal of Vascular Access ,2009 ,11-21.
Maki, et al.,In Vitro Studies of a Novel Antimicrobial Luer-Activated Needleless Connector for Prevention of Catheter-Related Blookstream Infection, Clinical Infection Diseases, vol. 50, Issue 12 ,Jun. 15, 2010 ,1580-1587.
Menyhay, et al.,Disinfection of Needleless Catheter Connecors and Access Ports with Alcohol May Not Prevent Microbial Entry: The Promise of a Novel Antiseptic-Barrier Cap, Infection control and Hospital Epidemiology, vol. 27 No. 1 ,Jan. 2006 ,23-27.
Stoker, et al.,One Less Problem, Safe Practrices when Administering IV Therapy, Managing Infection Control, 4 pgs ,Jun. 2008.
International Search Report and Written Opinion dated Jun. 22, 2018 for PCT/US2018/014237.

(56) References Cited

OTHER PUBLICATIONS

International Search Report and Written Opinion dated Feb. 1, 2017 for PCT/US2016/062061.
Office Action dated May 25, 2018 for U.S. Appl. No. 15/203,002.
Notice of Allowance dated Sep. 17, 2018 for U.S. Appl. No. 14/845,004.
Office Action dated Sep. 14, 2018 for U.S. Appl. No. 14/978,925.

DISINFECTING CAP FOR MEDICAL CONNECTORS

RELATED APPLICATION

The present application claims priority to provisional application No. 62/083,817, filed Nov. 24, 2014. This application is incorporated herein by reference in its entirety.

TECHNICAL FIELD

The present invention relates to caps for medical connectors, and more particularly to caps that can be used to protect the sterility of unconnected medical connectors, such as connectors that may be used for fluid flow or for fluid delivery systems.

BACKGROUND ART

Luer Access Valves (LAV), often referred to as Needless Injection Sites (NIS), are intended to be compliant with the ISO luer thread standard (ISO 594-2), but vary dimensionally, even within the standard. The ISO standard does not anticipate mating caps which lack a luer post—such as disinfecting caps. The problem is providing a secure fit which will not become loose with time and use. In a standard luer connection, the securement is provided by the locking taper fit of the male luer post in the female luer. In a disinfecting cap for an NIS, there is no luer post, and the securement must be provided by other features. In the design presented herein, the securement is provided by a compression fit of the inner diameter of the cap, and the major thread diameter of the NIS, as discussed in more detail below.

SUMMARY OF THE EMBODIMENTS

In accordance with one embodiment of the invention, a disinfecting cap is provided for accepting a needleless injection site and applying an antiseptic agent to the needleless injection site. The cap includes a cap body defining a chamber having an opening at a proximal end for accepting the needleless injection site, the chamber having a proximal portion and a distal portion. The cap also includes an antiseptic agent disposed in the distal portion of the chamber, and a breakable seal located in the chamber between the proximal and distal portions so as to be spaced away from the opening. The breakable seal prevents evaporation of the antiseptic agent until a needleless injection site is accepted into the cap. In one variation of this embodiment, the cap body includes a compliant wall about the proximal portion, and the compliant wall deforms when a needleless injection site is inserted into the opening so that the compliant wall engages threading elements on the outer diameter of the needleless injection site to removably hold the cap on the needleless injection site.

In one embodiment, the breakable seal is oriented transverse to, but not perpendicular to, a longitudinal axis of the cap. In an alternative embodiment, the breakable seal is oriented perpendicular to a longitudinal axis of the cap. In some embodiments, the cap also includes an absorbent material for holding the antiseptic agent, the absorbent material being disposed in the distal portion of the chamber. In some embodiments, the cap body includes a compliant wall about the proximal portion. The compliant wall deforms when a needleless injection site is inserted into the opening so that the compliant wall engages threading elements on the outer diameter of the needleless injection site to removably hold the cap on the needleless injection site. In some embodiments, the compliant wall is made of a thermoplastic elastomer. In alternative embodiments, the compliant wall is made of silicone.

In an alternative embodiment, a disinfecting cap is provided for accepting a needleless injection site and applying an antiseptic agent to the needleless injection site, wherein the cap body includes a compliant wall about the proximal portion, the compliant wall deforming when a needleless injection site is inserted into the opening so that the compliant wall engages threading elements on the outer diameter of the needleless injection site to removably hold the cap on the needleless injection site. The cap includes a chamber having an opening at the proximal end for accepting the needleless injection site, and an antiseptic agent disposed in the distal portion the chamber. The cap also includes a seal preventing evaporation of the antiseptic agent until a needleless injection site is accepted into the cap. In one variation of this embodiment, an absorbent material is included for holding the antiseptic agent, the absorbent material being disposed in the distal portion of the chamber.

In an alternative embodiment, a disinfecting cap is provided for accepting a needleless injection site and applying an antiseptic agent to the needleless injection site, wherein a flexible skirt extends from the cap body into the proximal portion, so that when a needleless injection site is inserted into the opening, the flexible skirt engages the outer diameter of the needleless injection site to removably hold the cap on the needleless injection site. The cap also include a cap body defining a chamber having an opening at the proximal end for accepting the needleless injection site, as well as an antiseptic agent disposed in the distal portion the chamber, and a seal preventing evaporation of the antiseptic agent until a needleless injection site is accepted into the cap. This embodiment may further include an absorbent material for holding the antiseptic agent, the absorbent material being disposed in the distal portion of the chamber.

In an alternative embodiment, a system is provided for disinfecting needleless injection sites, wherein the system includes a plurality of caps for accepting a needleless injection site and applying an antiseptic agent to the needleless injection site. Each cap includes a cap body defining a chamber having an opening at a proximal end for accepting the needleless injection site, the chamber having a proximal portion and a distal portion, an antiseptic agent disposed in the distal portion of the chamber, and a breakable seal located in the cavity between the proximal and distal portions so as to be spaced away from the opening, the breakable seal preventing evaporation of the antiseptic agent until a needleless injection site is accepted into the cap. The system also includes a carrier strip, wherein each of the plurality of disinfecting caps is removably attached at its proximal end to the carrier strip, so that the opening in each of the disinfecting caps is covered by the carrier strip. In a preferred embodiment, this carrier strip may further include projections, each projection shaped to engage the opening of a cap so that the cap is removably attached to the projection. In some embodiments, each cap is also removably attached to the carrier strip by adhesive.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions

Figure 2:
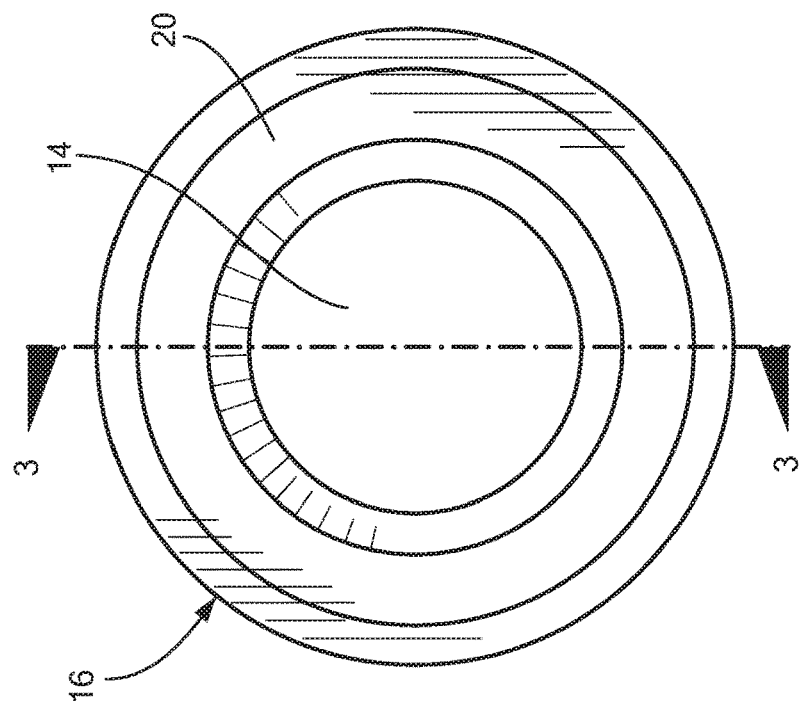
FIG. 2 is a proximal end view of the embodiment of FIG. 1.

As used in this description and the accompanying claims, the following terms shall have the meanings indicated, unless the context otherwise requires:

"NIS"—Needleless Injection Site (sometimes called LAV).

"LAV"—Luer Access Valve (also called NIS). A "LAV" is supposed to be made in conformity with industry standards for a luer. A NIS may be made in conformance with industry standards for a luer, but may not be; instead the NIS may be made in conformance with a manufacturer-specific, non-industry-standard specification.

The terms "proximal" and "distal," when used herein relative to a cap, are such that an NIS or LAV is inserted into a proximal end of the cap and advanced toward a distal end of the cap.

"Elastomer" or "Elastomeric"—Materials that are highly elastic. When deformed, they are able to return to near their original shape. Deformations are not permanent. Rubber and silicones are examples of elastomers.

"Malleable"—Materials which are easily deformed, and once deformed hold much of the deformed shape. Malleable materials do not return to near their original shape.

"Compliant"—An elastomeric or malleable material that, when pressed against a contoured or shaped surface, conforms substantially to that surface.

"Flexible"—A material that easily bends. A flexible material need not be elastomeric or malleable.

"Breakable"—A breakable seal may be pierced, punctured, torn, ruptured or the like so as to permit fluid communication from one side of the seal to the other.

"Absorbent"—a material capable of holding or storing an antiseptic agent.

"Reservoir"—a volume capable of receiving and holding/storing an antiseptic agent.

Preferred embodiments of the invention provide a disinfecting cap for an NIS/LAV include the following features:

A threadless flexible portion (the engagement region), near the proximal end of the cap, for engaging the threads of the NIS/LAV and securing the cap to the NIS/LAV. Alternatively, a malleable portion for engaging the threads is provided as the engagement region. In another alternative embodiment, a flexible skirt is provided at or near the cap's opening at the proximal end of the cap for securing the NIS/LAV.

A reservoir of liquid, gel, or paste disinfectant, such as isopropyl alcohol (IPA). The reservoir, located in a distal portion of the cap's interior chamber, may include an absorbent material for holding the disinfectant, and in some embodiments, scrubbing the face of the NIS/LAV.

A breakable or frangible seal for the reservoir which is broken or unsealed upon installation of the cap on the NIS/LAV. In one embodiment, the seal is located in the cap's interior chamber away recess from the cap's opening.

Mating features may be provided on opposing ends of the caps for joining the caps into a stack or chain prior to use. The mating engagement may be used to provide sterility of the engagement portion of the caps.

A number of illustrative embodiments are presented herein. FIGS. 1-6 show views of one embodiment of a cap according to the invention.

Figure 1:
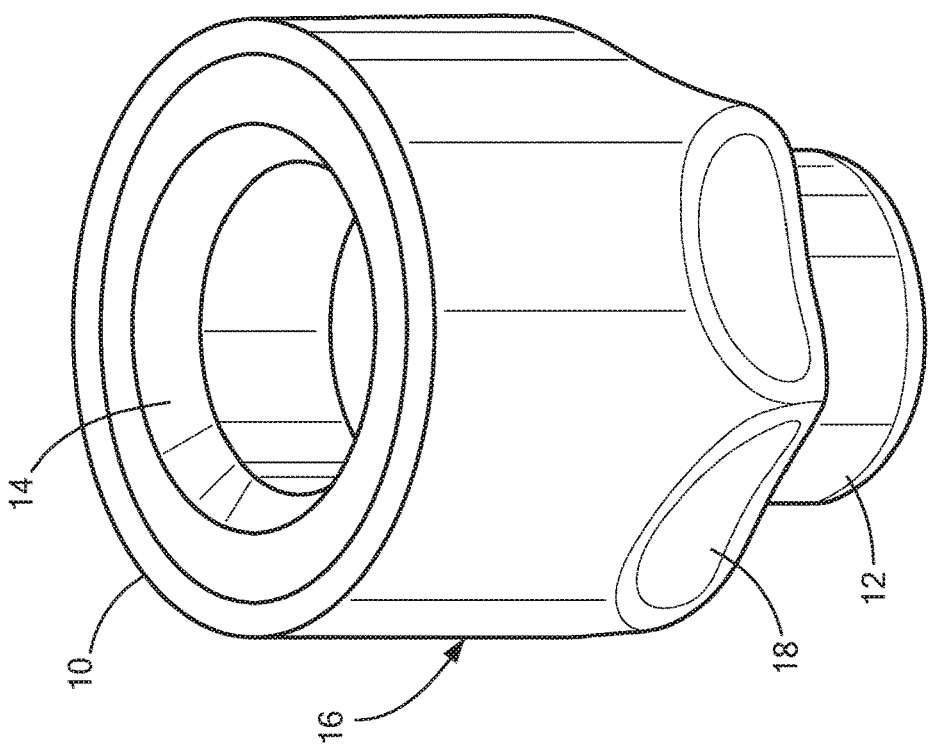
FIG. 1 is a perspective view of an embodiment of the invention.

FIG. 1 is a perspective view of a disinfecting cap. The cap has a proximal end 10 and a distal end 12. An opening 14 accepts a NIS to be disinfected. The cap includes a cap body 16 that extends from the proximal end 10 to the distal end 12. Near its distal end 12, the cap body 16 includes a gripping area 18, which may be formed by a ring of scallops around the circumference of the cap body 16, as shown in FIG. 1.

Figure 3:
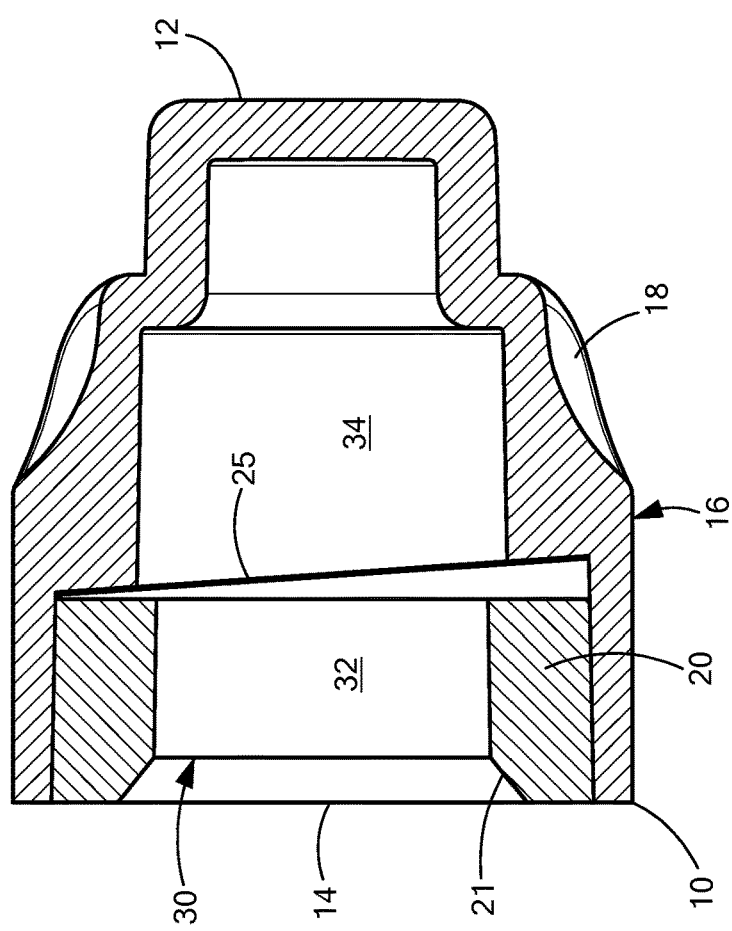
FIG. 3 is a sectional view taken along line C-C of FIG. 2.

FIG. 2 shows a proximal end view of the cap of FIG. 1. The opening 14 and the proximal edge of the cap body 16 are shown in FIG. 2. Also shown in FIG. 2 is the proximal edge of compliant wall 20, which surrounds the opening 14. FIG. 3 is a sectional view of the FIG. 1 cap taken along line C-C in FIG. 2.

As shown in FIG. 3, the cap body 16 defines a chamber 30, which has only a single opening 14 to the exterior of the cap. The chamber 30 has a proximal portion 32 and a distal portion 34. Between these two portions is a breakable seal 25. The breakable seal 25 keeps antiseptic liquid in the distal portion 34 and keeps the antiseptic liquid from evaporating until the seal 25 is broken, which occurs when an NIS is fully inserted into the cap. This distal portion 34 may be referred to as a reservoir; this reservoir is enclosed by the side walls of the cap body 16, by the closed end of the cap body, and by the breakable seal 25.

The breakable seal 25 is preferably disposed at an angle from the perpendicular to the longitudinal axis of the cap. This angle makes it easier for the NIS to break through the seal 25. The seal 25 may be of any one of a variety of materials capable of suitably inhibiting the loss of disinfectant over the shelf life of the cap. Materials envisioned for the breakable seal 25 may include, but are not limited to, metal foils and polymer sheets. Sheet and foil materials may be bonded through adhesives or welding to the cap.

The breakable seal 25 is broken—releasing the stored disinfectant—when the NIS is installed sufficiently far into the cap. The disinfectant then disinfects the exterior surface of the NIS. Foils and sheets may be chosen such that they are weak enough to break when forced by the NIS. Foils and sheets may also be scored or otherwise selectively weakened so as to improve their ability to break. The bond or weld of the foil or sheet to the cap body may also be configured to break under the force of the NIS.

Also, as shown in FIG. 3, the compliant wall 20 has a beveled inner edge 21 at the opening 14, which helps guide the NIS into the chamber 30. The region of the compliant wall 20 may be referred to as a thread-engagement region. This thread-engagement region may be made of an elastomeric or malleable material. This region is designed to engage the threads of the NIS. This thread-engagement region may be smooth inside having no threads. Upon engagement with the NIS, this thread-engagement region may deform to accommodate the thread of the NIS. The fit is similar to that of an elastomeric hose or tube on a pipe nipple or hose barb.

Figure 4:
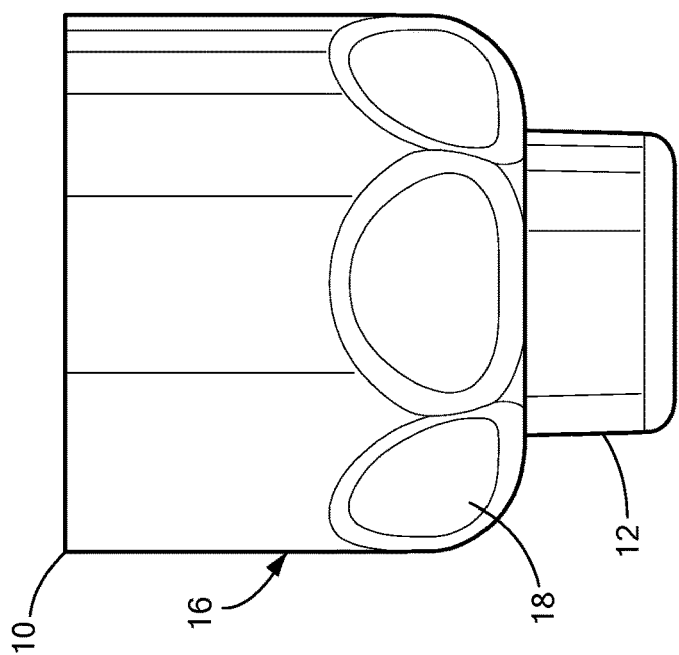
FIG. 4 is a first side view of the embodiment of FIGS. 1-3.
Figure 6:
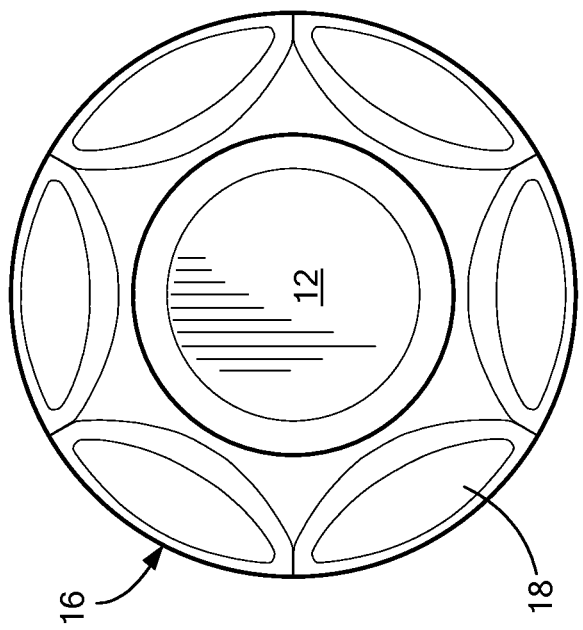
FIG. 6 is a distal end view of the embodiment of FIGS. 1-5.
Figure 5:
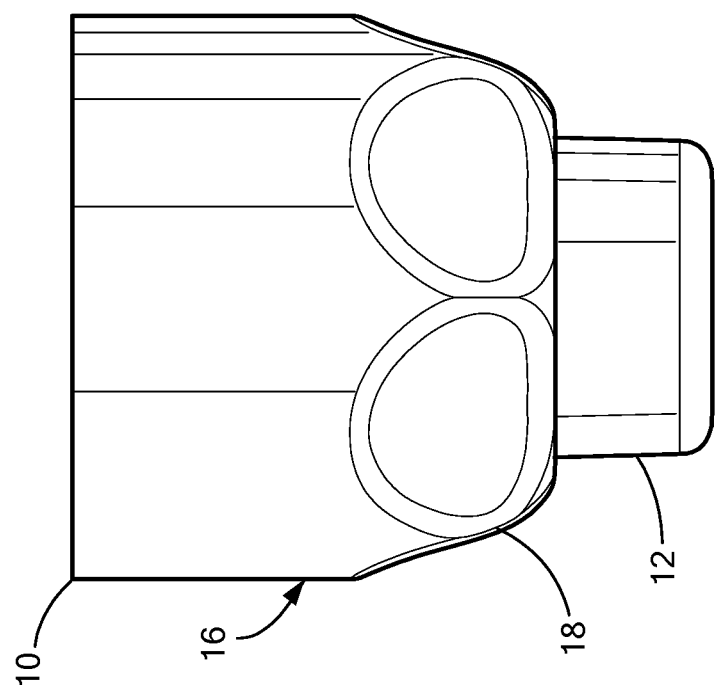
FIG. 5 is a second side view of the embodiment of FIGS. 1-4

FIGS. 4 and 5 show alternative side views of the cap, and FIG. 6 shows a distal end view of the cap.

Figure 7:
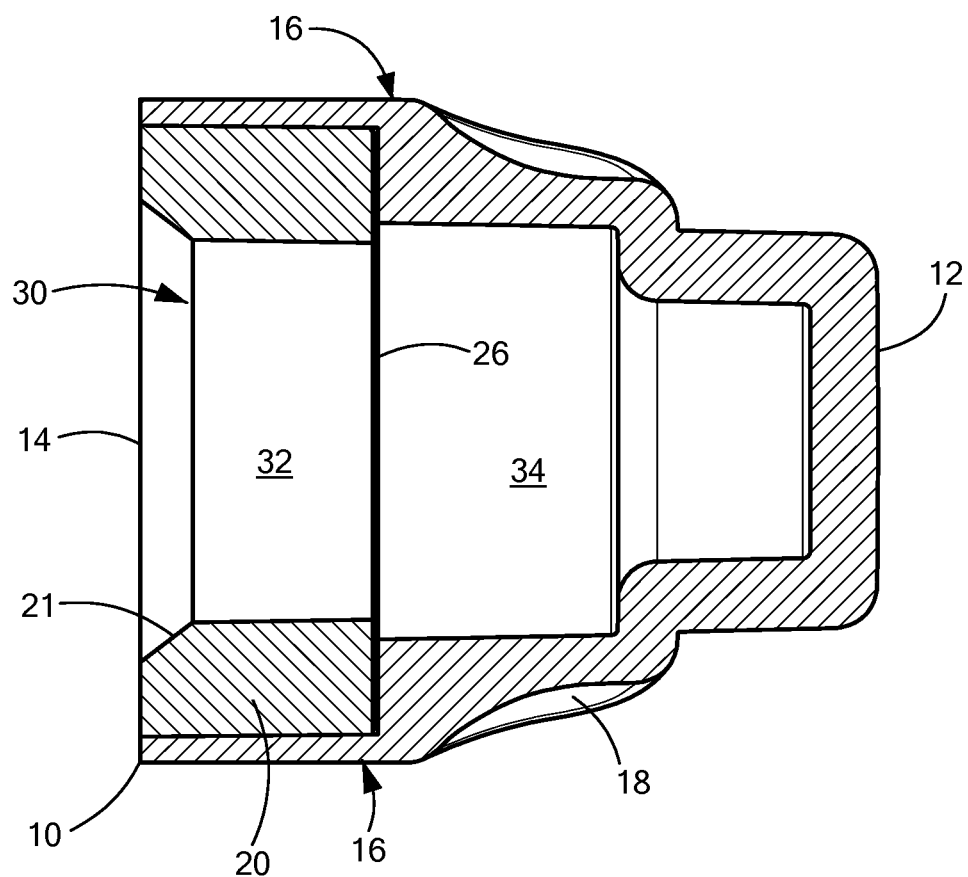
FIG. 7 is a sectional view of an alternative embodiment with a breakable seal oriented perpendicular to the longitudinal axis of the cap.

FIG. 7 is a sectional view of an alternative embodiment that is similar to the embodiment of FIGS. 1-6 but has a breakable seal 26 that is oriented perpendicular to the longitudinal axis of the cap, instead of the angled seal 25 shown in FIG. 3. Like the embodiments of FIGS. 1-6, the FIG. 7 embodiment includes a cap body 16 that defines a chamber 30 having an opening 14 at a proximal end 10 for accepting the needleless injection site. The FIG. 7 chamber 30 also has a proximal portion 32 and a distal portion 34, with an antiseptic agent disposed in the distal portion 34. The breakable seal 26 is located in the chamber 30 between the proximal and distal portions. The breakable seal 26 prevents evaporation of the antiseptic agent until a NIS is accepted into the cap and breaks through the seal 26. Also, like the embodiment of FIGS. 1-6, the FIG. 7 embodiment includes a compliant wall 20 near the opening 14. This compliant wall 20 deforms when a NIS is inserted into the opening 14 so that the compliant wall 20 engages threading elements on the outer diameter of the NIS. This arrangement allows the cap to be removably held on the NIS. In the FIG. 7 embodiment, the distal end 12 of the cap body 16 is closed off, so that the cap has only a single opening 14. The FIG. 7 cap body 16 also includes a gripping portion 18.

In an alternative embodiment, a moveable seal may be used instead of the breakable seal. For example, the seal may be a disk having some thickness such that it behaves like a stopper or piston sealing against the sidewalls of the cap body. In the case of a disk/piston/stopper style of seal, it is preferable that at least one of the components—the moveable seal or the interior sidewall of the cap be elastomeric to better inhibit disinfectant loss. Disk/piston/stopper designs may be configured such that the disk is held in place by friction (increased by elastomeric fits). The force of installation of the NIS is sufficient to overcome the friction of the disk, thereby moving the disk to a position where the fluid communication with the distal portion is established. Adhesives or welds may also be used to augment a disk/piston/stopper design.

In alternative embodiments, the openings 14 of the caps shown in FIGS. 1-7 are closed to maintain sterility prior to use. This may be achieved, for example, by: (i) placing the cap in additional packaging, (ii) adding an adhesive or welded lid of a material such as foil, polymer, paper, "Tyvek®"-type material, etc., i.e., a secondary seal, or (iii) creating a stopper-like mating fitment between caps, as discussed below. A male member may be configured on the closed distal end 12 of each cap which mates with the opening 14 of another cap. A chain or column of caps may then be formed, each subsequent cap assuring sterility of the mated cap. A dedicated or dummy cap must be provided to close the opening 14 of the last cap in the chain. The last cap in the chain could also be closed by any of the other closure means discussed above.

Figure 9:
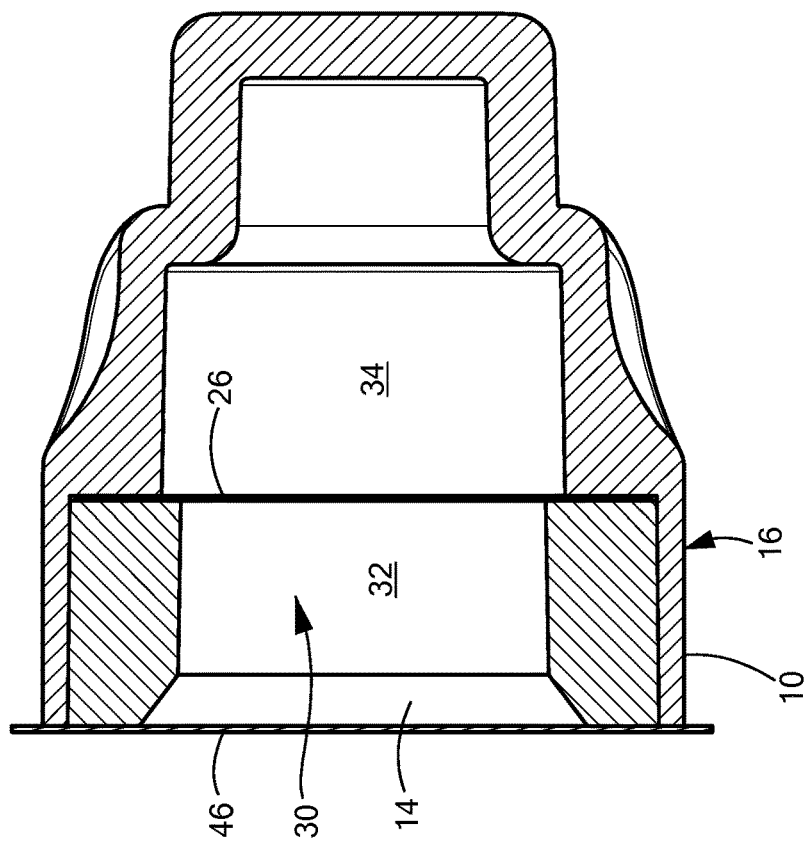
FIG. 9 is a sectional view of the FIG. 8 embodiment.
Figure 8:
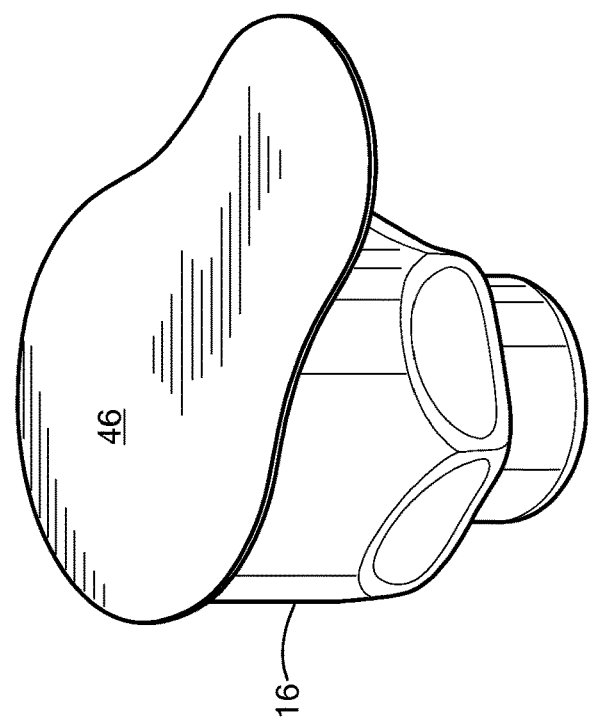
FIG. 8 is a perspective view of an alternative embodiment with a secondary seal.

FIG. 8 shows a disinfecting cap with a secondary seal 46. FIG. 9 shows a sectional view of the FIG. 8 embodiment. Like the FIG. 7 embodiment, the embodiment of FIGS. 8 and 9 includes a cap body 16 with an opening 14 at the proximal end 10, a chamber 30 defined by the cap body 16. The chamber is divided into a proximal portion 32 and a distal portion 34 by a breakable (primary) seal. A secondary seal 46 covers the opening. The secondary seal 46 prevents contaminants from entering the proximal portion 32 of the chamber 30 during shipment and storage. Just before use, the secondary seal 46 is removed from the cap, and then the cap is placed on an NIS causing the breakable seal 26 to be ruptured and releasing the antiseptic liquid to disinfect exterior surfaces of the NIS. The cap is left on the NIS long enough to allow the antiseptic liquid to disinfect the NIS or until the NIS is ready for use.

Figure 10:
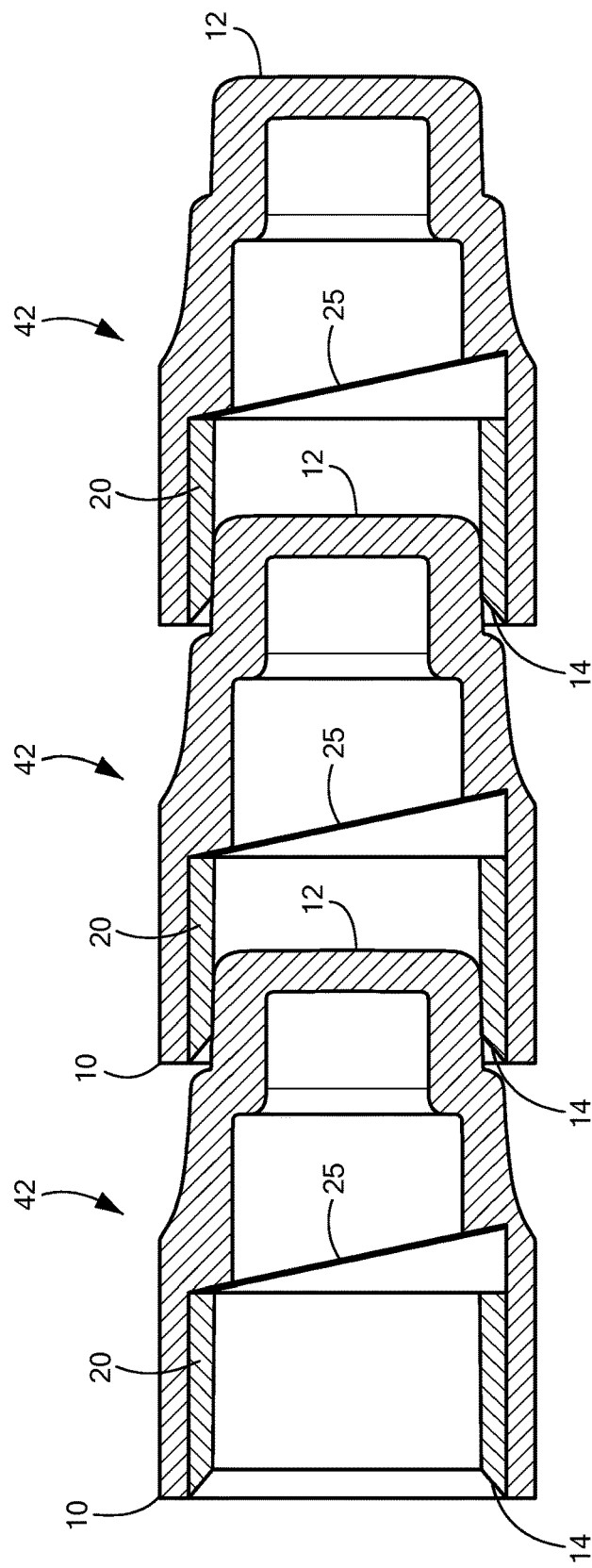
FIG. 10 is a sectional view of a stacked arrangement of caps.
Figure 11:
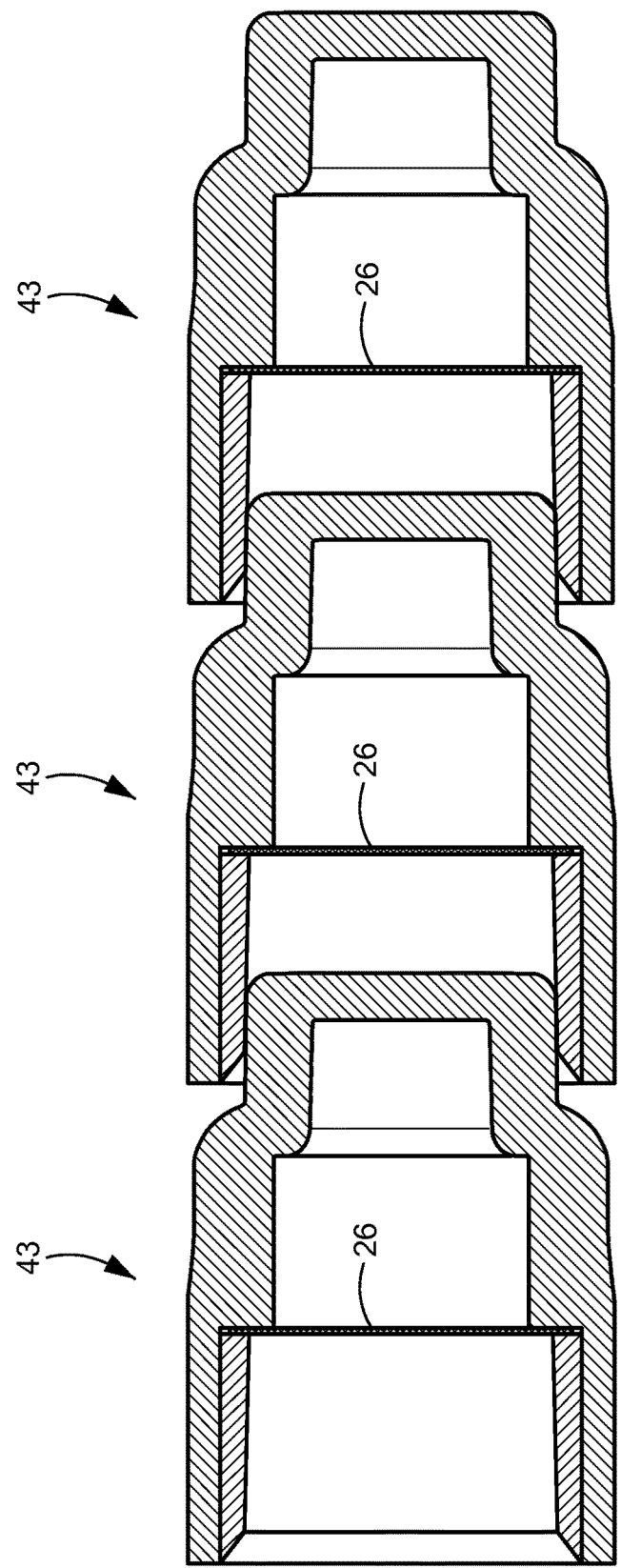
FIG. 11 is a sectional view of an alternative embodiment of a stacked arrangement of caps.

FIG. 10 is a sectional view of a stacked arrangement of three caps 42. The distal end 12 of one cap fits into the opening 14 in the proximal end 10 of the next cap, the compliant wall 20 of which holds the first cap. In the FIG. 10 embodiment, the caps 42 have breakable seals 25 that are oriented at an angle to the perpendicular to the longitudinal axis of the caps. FIG. 11 is a sectional view of a stacked arrangement of similar caps 43. In the FIG. 11 embodiment, the caps 43 have breakable seals 26 that are oriented perpendicular to the longitudinal axis of the caps.

Figure 12:
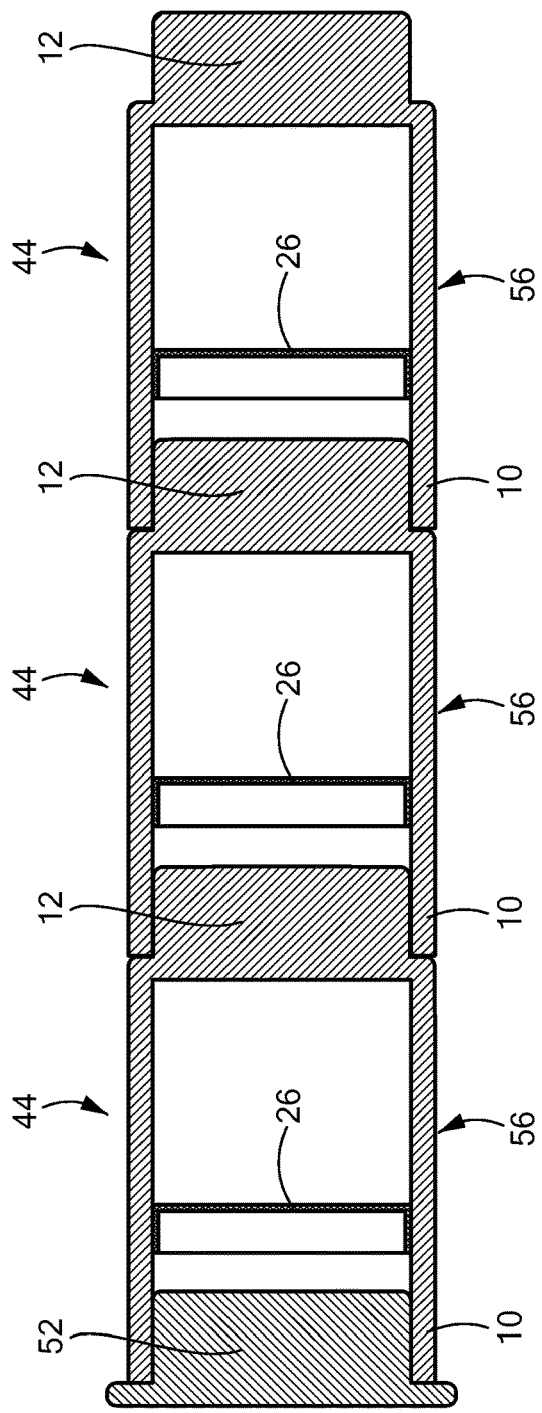
FIG. 12 is a sectional view of another alternative embodiment of a stacked arrangement of caps.
Figure 13:
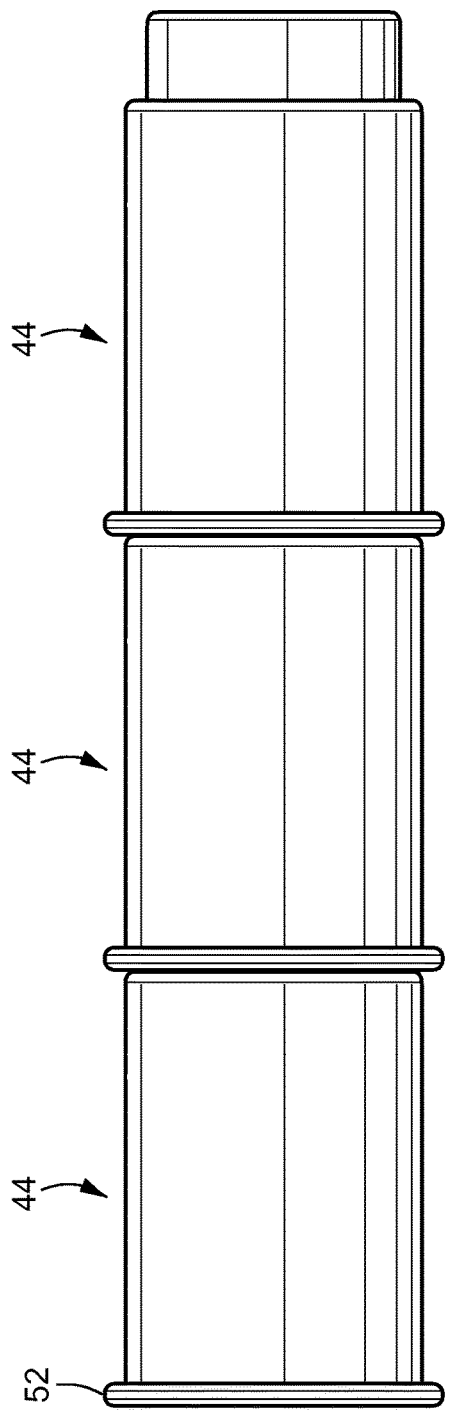
FIG. 13 is a side view of the embodiment of FIG. 12.

FIG. 12 is a sectional view of alternative embodiment of a stacked arrangement of caps 44. As in the embodiments of FIGS. 10 and 11, the cap bodies 56 are shaped so that the distal end 12 of one cap is received into the proximal end 10 of the next cap. A stopper 52 is used to cover the open proximal end 10 of the first cap. In these caps 44, the breakable seal 26 is oriented perpendicular to the longitudinal axis of the cap 44. FIG. 13 is a side view of the caps 44 and the stopper 52 of the embodiment of FIG. 12.

Figures 14, 15:
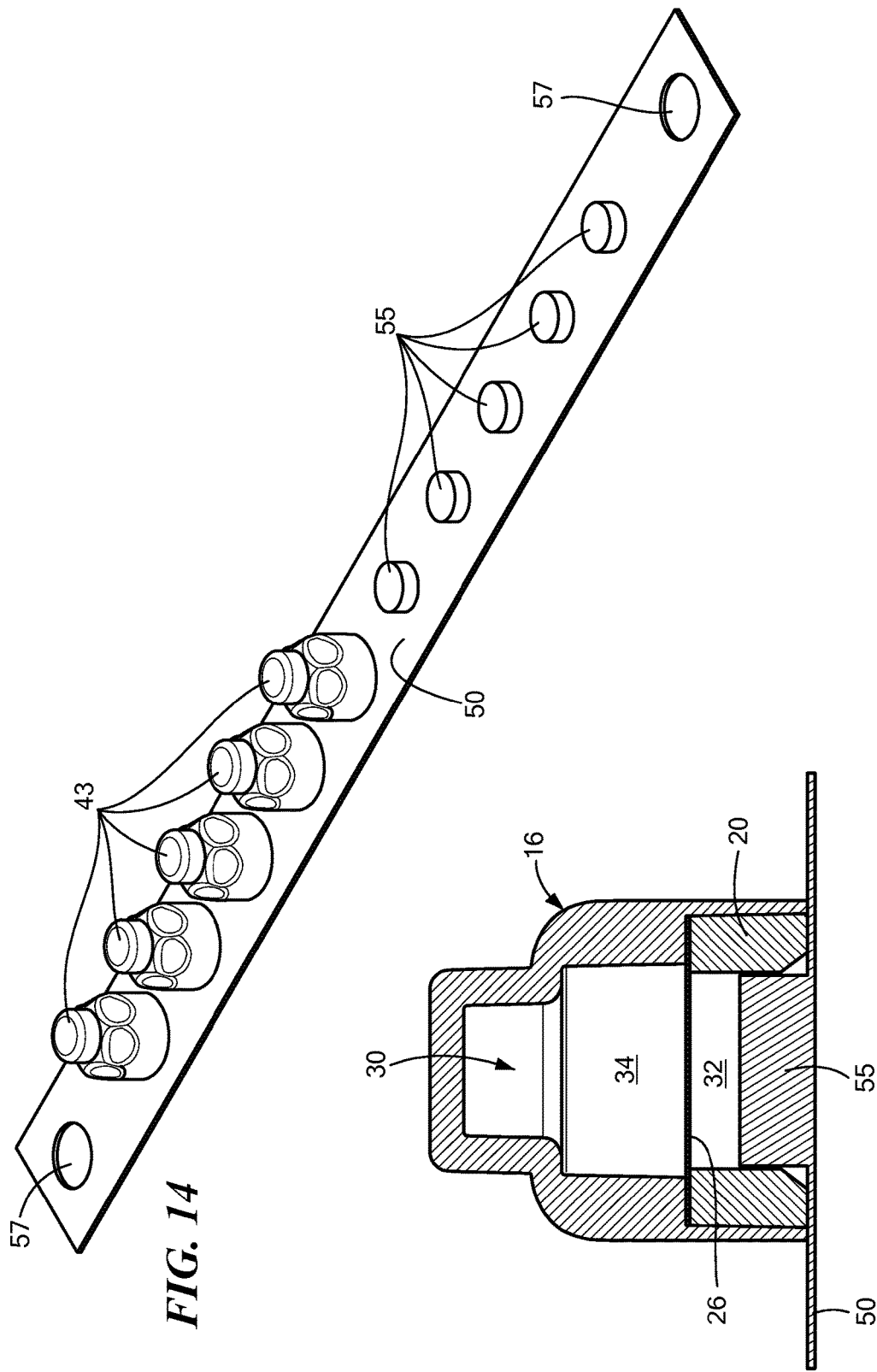
FIG. 14 is a perspective view of an embodiment of a carrier strip for holding a plurality of caps.
FIG. 15 is a sectional view of the FIG. 14 embodiment.

FIG. 14 shows an embodiment of a carrier strip 50 for holding a plurality of caps 43, and FIG. 15 is a sectional view of the FIG. 14 embodiment. In this embodiment, the carrier strip 50 includes a plurality of button-shaped protrusions 55, each of which is adapted to retain a cap 43. As can be seen in FIG. 15, the buttons 55 are shaped and sized to fit snugly into the proximal portion 32 of the cap's chamber 30. Preferably, the button 55 interferes sufficiently with the cap's compliant wall 20 so that the cap 43 is friction fitted to the button 55. In this way, a plurality of caps 43 may be held on a single strip 50, so that each cap 43 may be easily removed and used by a healthcare professional. This friction fit of the cap 43 to the strip 50 may be supplemented by adhesive that helps hold the cap more securely to the strip, but nevertheless permits the easy removal of the cap from the stip. Alternatively, adhesive may be used in lieu of the buttons altogether to removably hold the caps 43 to the strip 50. The carrier strip 50 may also be provided with a hole or holes 57 to permit the carrier strip 50 to be hung from an IV pole or the like, so that the caps 43 may be readily accessible near where they are to be used. In addition to holding the cap 43 to the strip 50, the projections 55 also keep possible contaminants out of the proximal portion 32 of the chamber 30. The antiseptic liquid is kept in the distal portion 34 until the cap 43 is placed on an NIS, causing the NIS to break through the seal 26, resulting in the surface of the NIS being disinfected by the antiseptic liquid.

Figure 16:
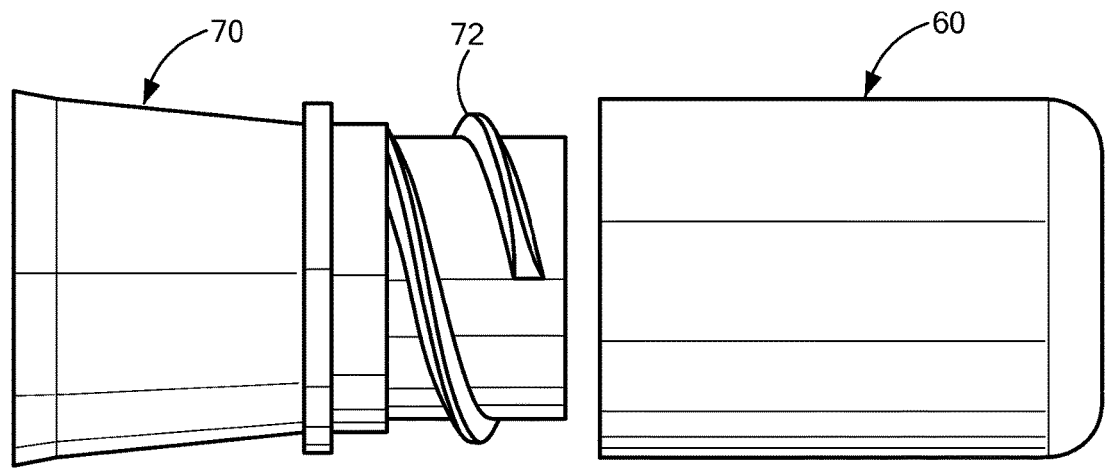
FIGS. 16-18 are side views of a disinfecting cap according to the present invention being installed on a needleless access site.
Figure 17:
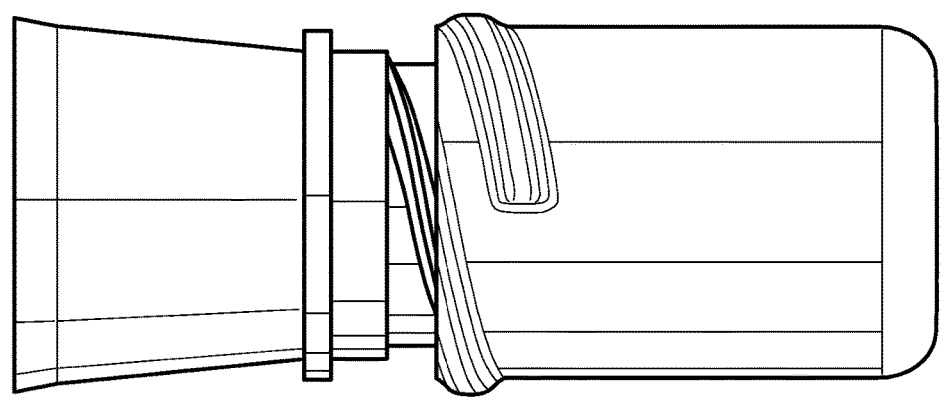
Figure 18:
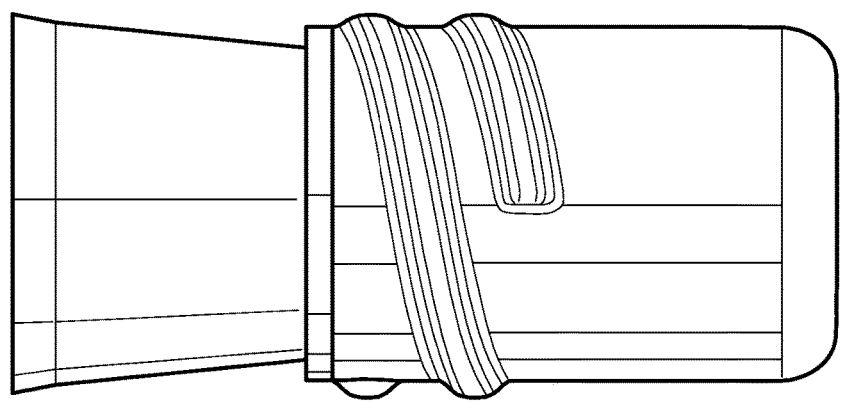
Figure 19:
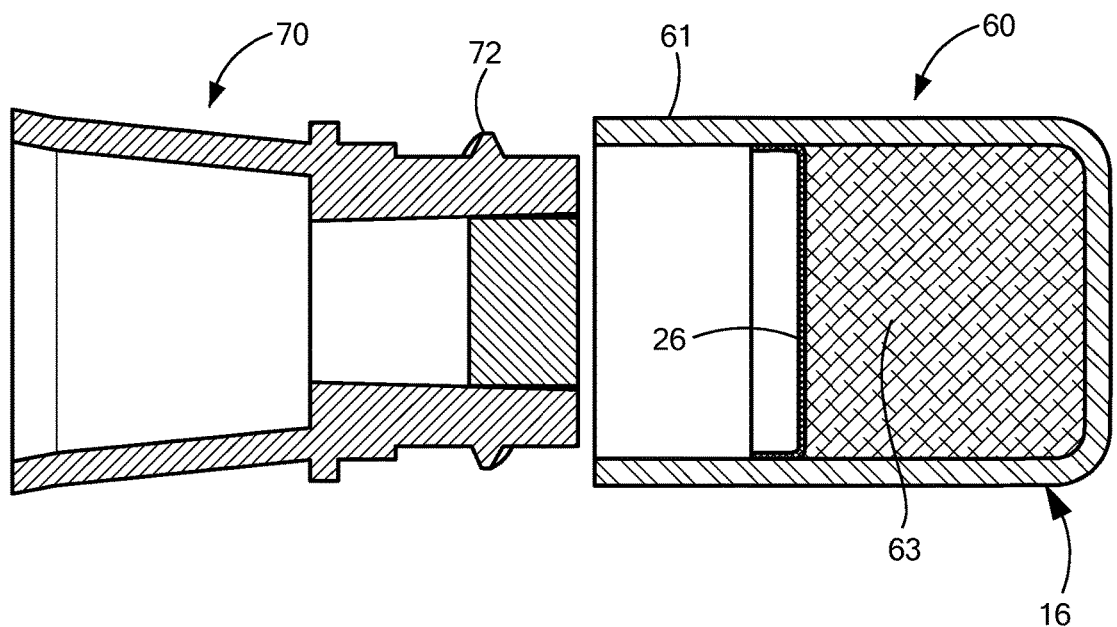
FIGS. 19-21 are sectional views of the cap and needleless access site of FIGS. 16-18.
Figure 20:
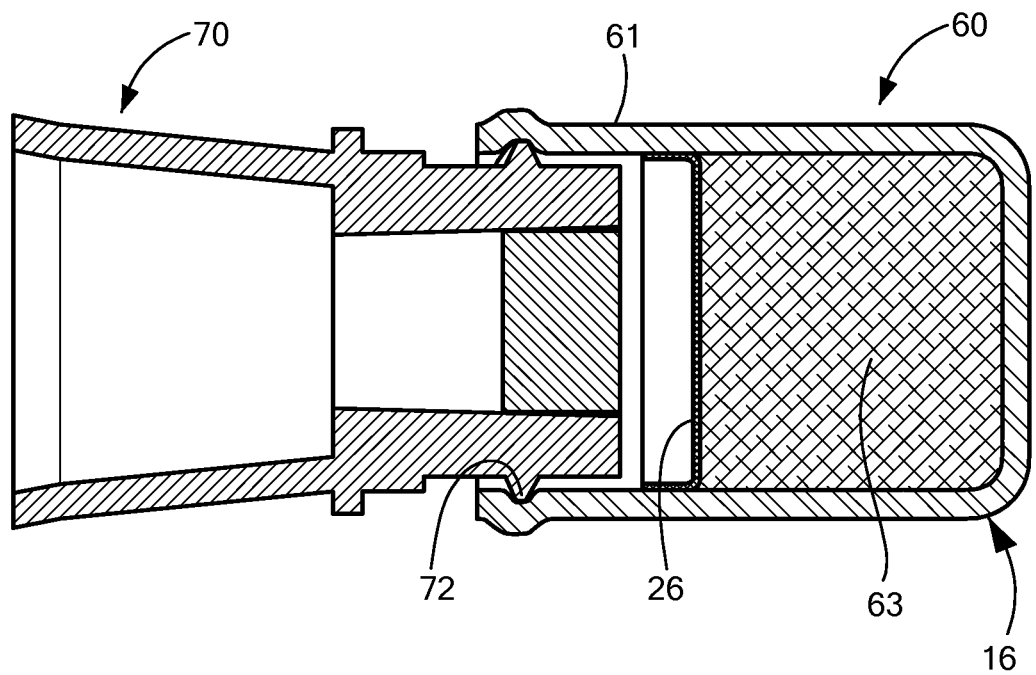
Figure 21:
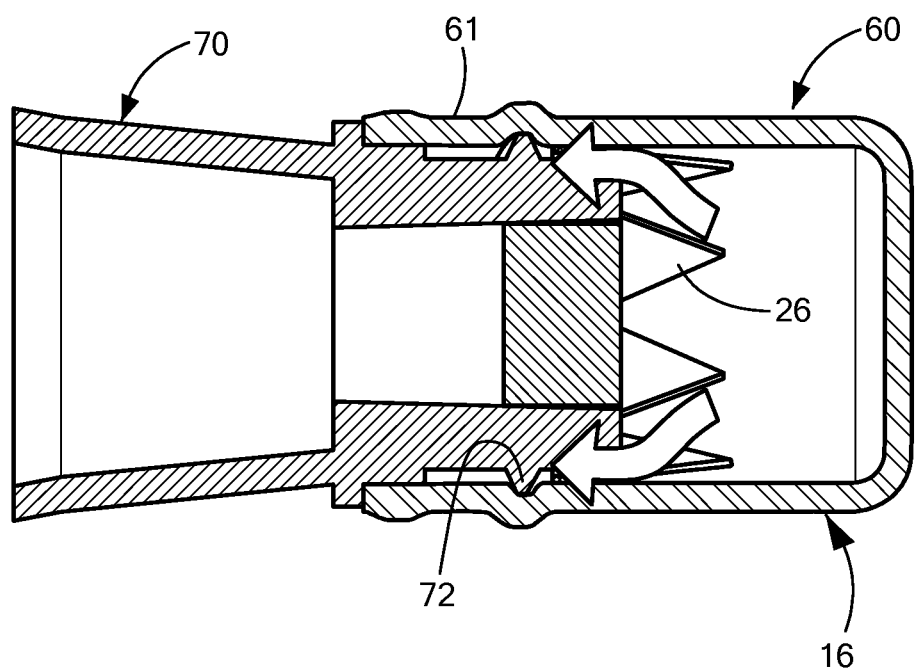

FIGS. 16-18 are side views of a cap 60 being installed on a needleless access site 70, and FIGS. 19-21 are sectional views of the same process. In FIGS. 16 and 19, the cap 60 and the NIS 70 are brought near each other; in FIGS. 17 and 20, the NIS 70 has started being inserted into the cap 60; and in FIGS. 18 and 21, the cap 60 is fully installed on the NIS 70. When the cap 60 is fully on the NIS 70, the seal 26 is broken and the antiseptic liquid disinfects the exposed surfaces of the NIS 70. The white arrows shown in FIG. 21 show how the antiseptic liquid can flow from the distal portion around the edge of the NIS 70 so as to disinfect the sides as well as the face of the NIS.

FIGS. 19 and 20 show an absorbent pad 63 for holding the antiseptic liquid. In a preferred embodiment, the NIS 70 comes into contact with the absorbent pad 63 when fully inserted into the cap 60. The absorbent pad is not included in FIG. 21, so that the broken seal 26 can be more easily seen.

In this embodiment, the entire cap is monolithically formed as a single part, a compliant material. As can be seen in FIGS. 16-21, the threads 72 on the NIS 70 are accommodated by a compliant wall 61, which is in the thread engagement region of the cap body 16. The cap body 16, including the compliant wall 61, may be made of a silicone or a thermoplastic elastomer (for example, Santoprene). The compliant wall 61 bulges out where the threads 72 of the NIS come into contact with inner surface of the compliant wall. In FIGS. 17 and 20, the threads 72 have begun to engage the compliant wall 61, but the NIS has not yet come into contact with the breakable seal 26. In FIGS. 18 and 21, the threads 72 are more fully engaged by the compliant wall 61, and the NIS has broken through the seal 26.

Figure 22:
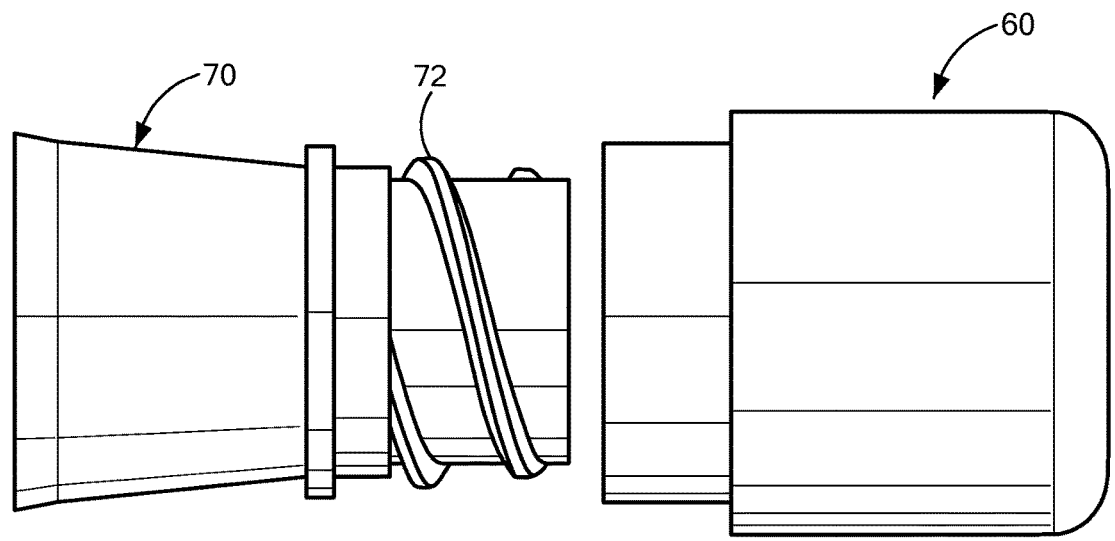
FIGS. 22-24 are side views of an alternative disinfecting cap according to the present invention being installed on a needleless access site.
Figure 23:
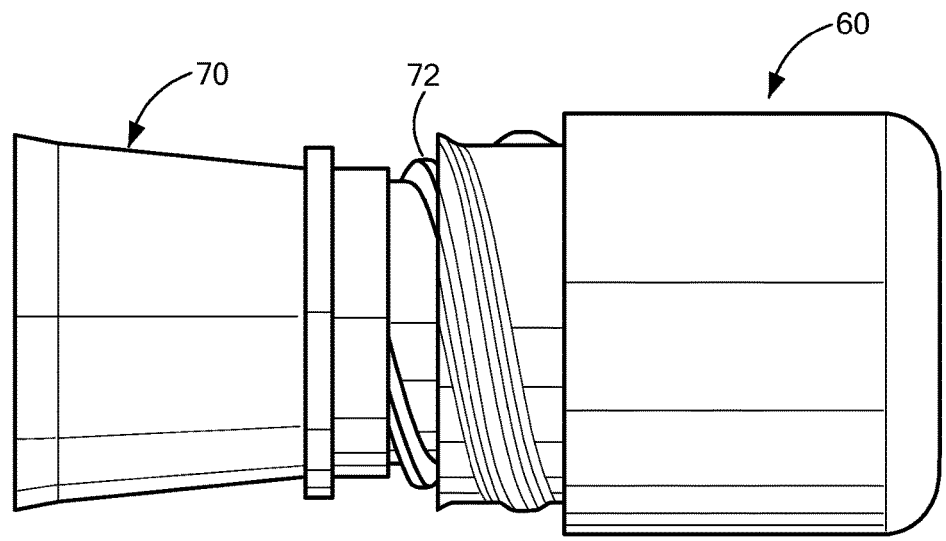
Figure 24:
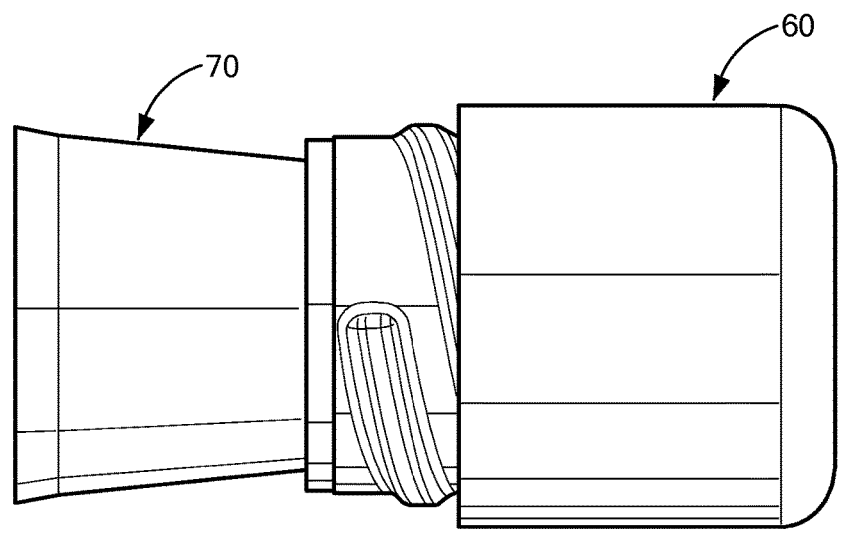
Figure 25:
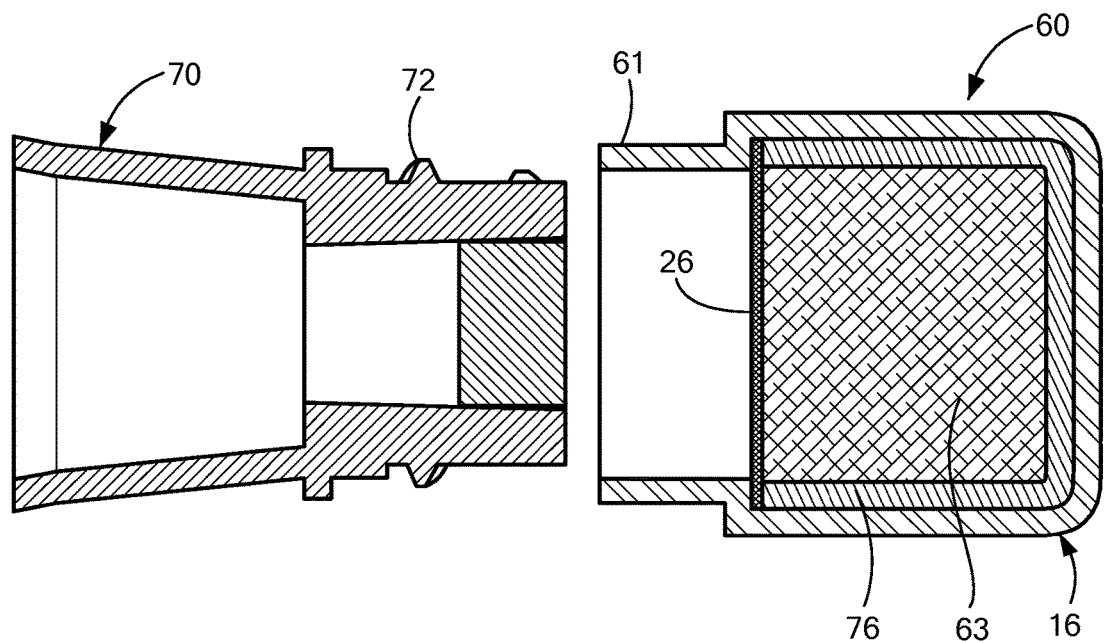
FIGS. 25-27 are sectional views of the cap and needleless access site of FIGS. 22-24.
Figure 26:
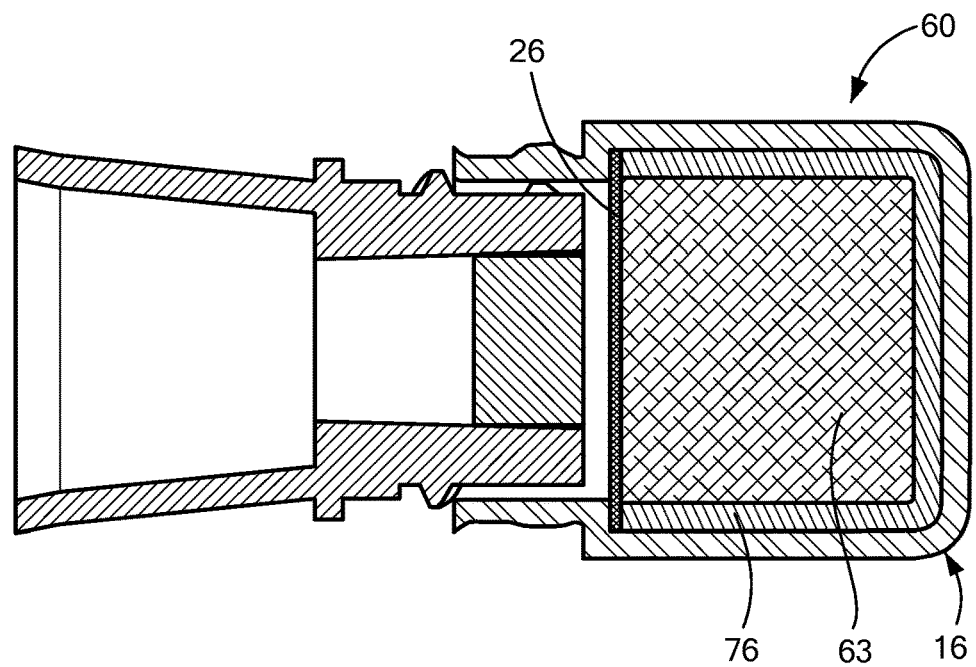
Figure 27:
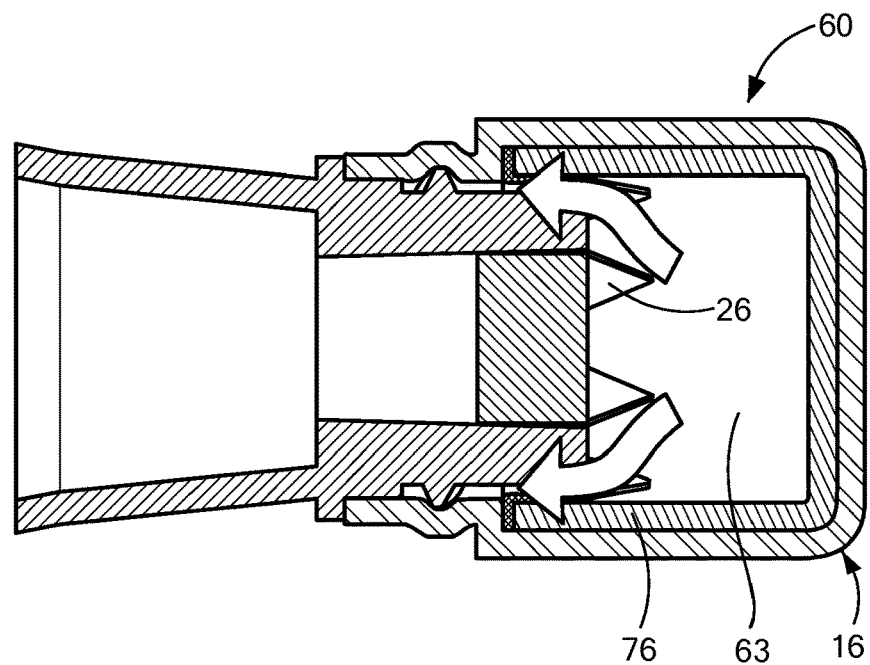

FIGS. 22-24 are side views of an alternative cap 60 being installed on a needleless access site 70, and FIGS. 19-21 are sectional views of the same process. In this embodiment, a reservoir 76 for holding the antiseptic liquid—preferably with an absorbent material 63 as shown in FIGS. 25-27—is a separate part which is inserted into the cap 60. In some embodiments, the cap 60 is made of an elastomeric material. The material of the cap body 16 also forms the thread engagement region or compliant wall 61. In this embodiment, the materials of the reservoir 76 and the thread engagement region may be selected separately.

Selecting the reservoir and thread engagement region materials separately allows the materials to be optimized for the requirements of each region or component. For example, an IPA impermeable material may be chosen for the reservoir (such as polypropylene), while an elastomer might be chosen for the thread engagement region (such as a thermoplastic polyurethane, for example, Tecothane® or Pellethane®). The elastomer of the thread engagement region may have less resistance to IPA, but the elastomeric properties are more suitable to the requirements of the thread engagement region. Additionally, this construction allows a soft feel or grip to the outside of the cap while providing structure or support to the body of the cap by the reservoir, which may be constructed of a more rigid material. The separate reservoir might be filled and closed prior to assembly with the cap.

In FIGS. 22 and 25, the cap 60 and the NIS 70 are brought near each other; in FIGS. 23 and 26, the NIS 70 has started being inserted into the cap 60; and in FIGS. 24 and 27, the cap 60 is fully installed on the NIS 70. When the cap 60 is fully on the NIS 70, the seal 26 is broken and the antiseptic liquid disinfects the exposed surfaces of the NIS 70. FIGS. 25 and 26 show an absorbent pad 63 for holding the antiseptic liquid. In a preferred embodiment, the NIS 70 comes into contact with the absorbent pad 63 when fully inserted into the cap 60. The absorbent pad is not included in FIG. 27, so that the broken seal 26 can be more easily seen. As can be seen in FIGS. 22-27, the threads 72 on the NIS 70 are accommodated by a compliant wall 61, which is in the thread engagement region of the cap body 16. The compliant wall 61 bulges out where the threads 72 of the NIS come into contact with inner surface of the compliant wall. In FIGS. 23 and 26, the threads 72 have begun to engage the compliant wall 61, but the NIS has not yet come into contact with the breakable seal 26. In FIGS. 24 and 27, the threads 72 are more fully engaged by the compliant wall 61, and the NIS has broken through the seal 26. The white arrows shown in FIG. 27 show how the antiseptic liquid can flow from the distal portion around the edge of the NIS so as to disinfect the sides as well as the face of the NIS.

Figure 28:
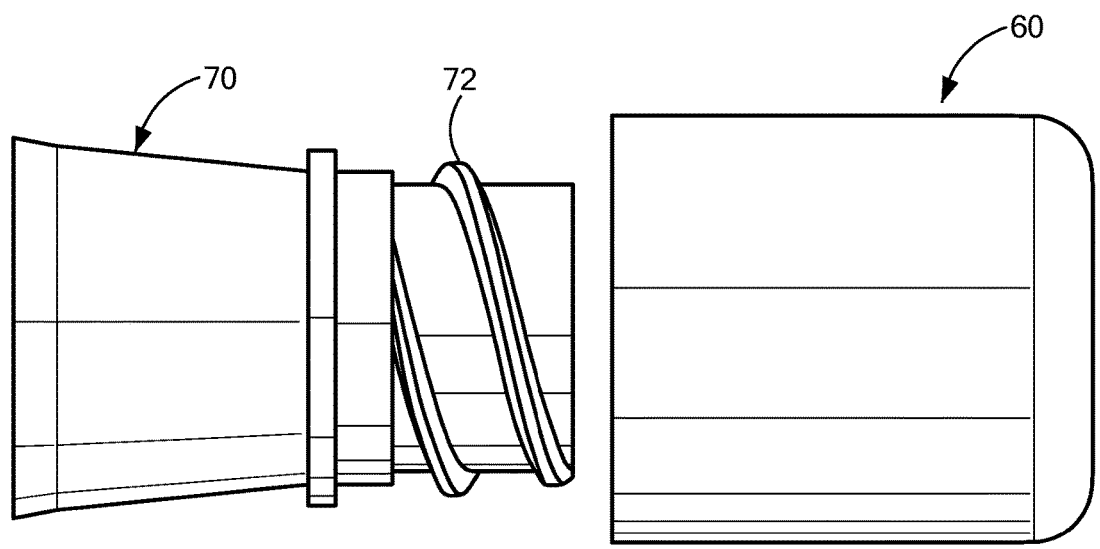
FIGS. 28-30 are side views of an alternative disinfecting cap according to the present invention being installed on a needleless access site.
Figure 29:
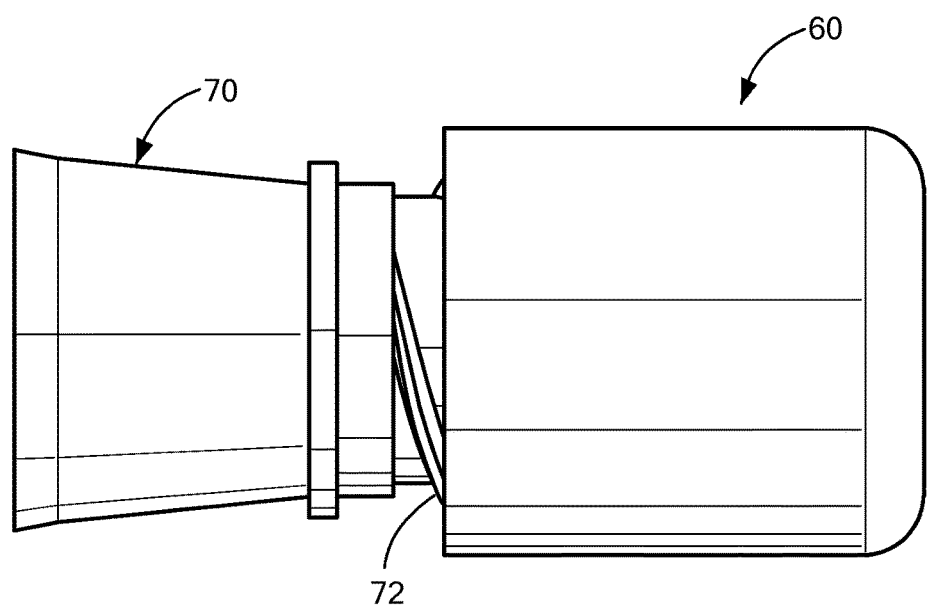
Figure 30:
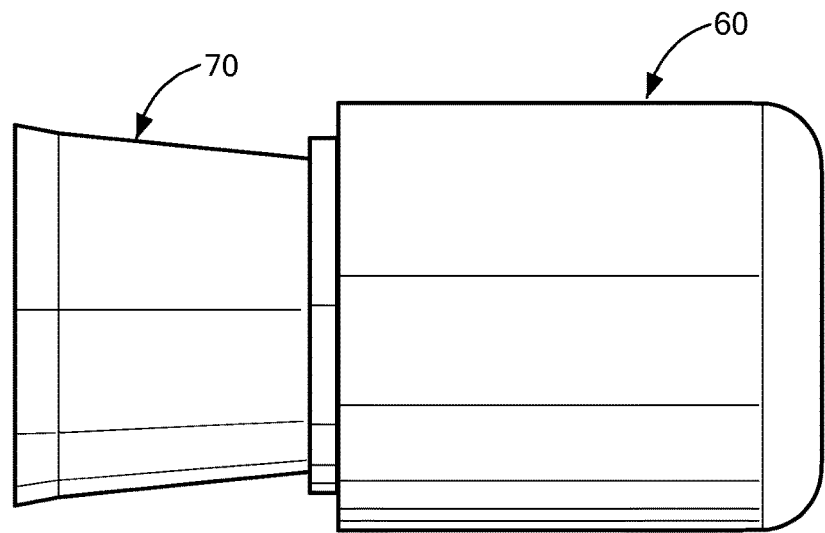
Figure 31:
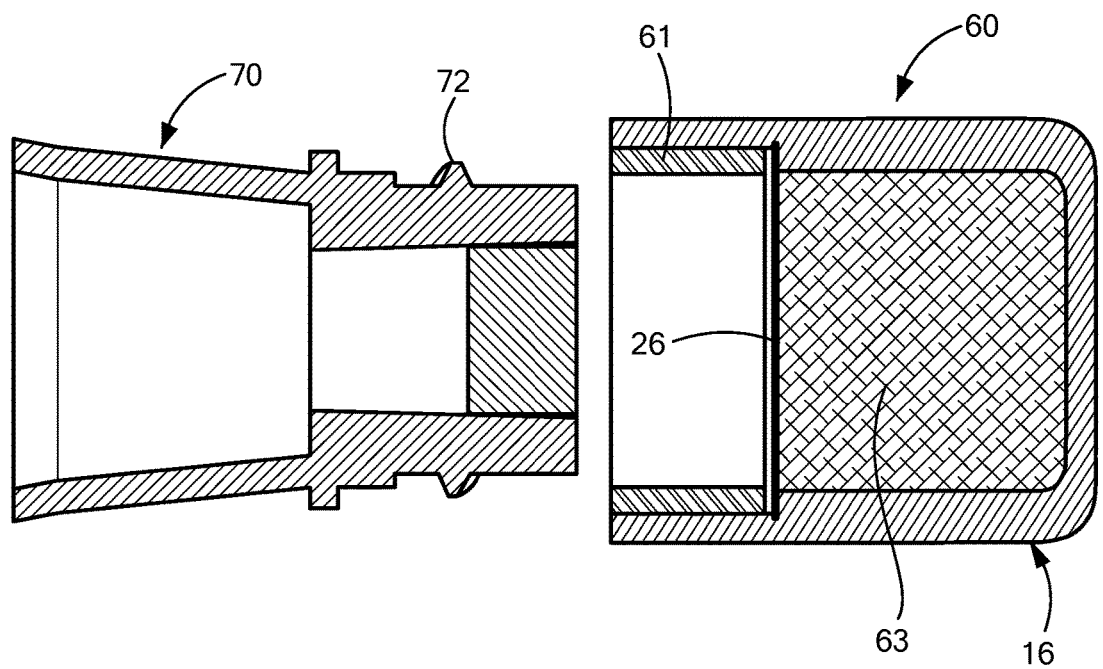
FIGS. 31-33 are sectional views of the cap and needleless access site of FIGS. 28-30.
Figure 32:
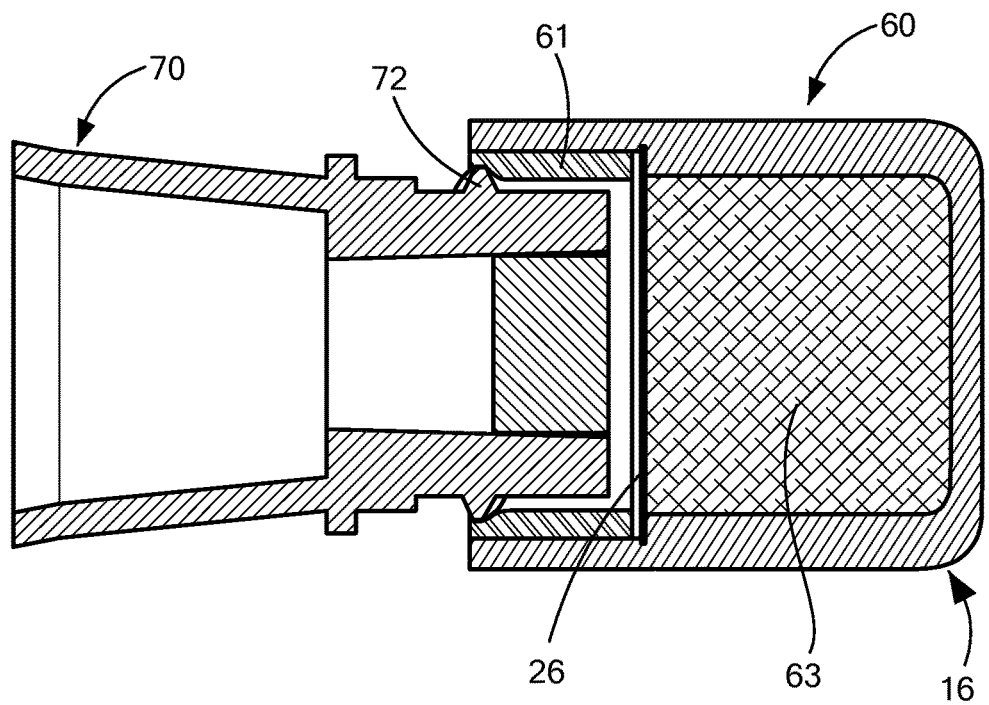
Figure 33:
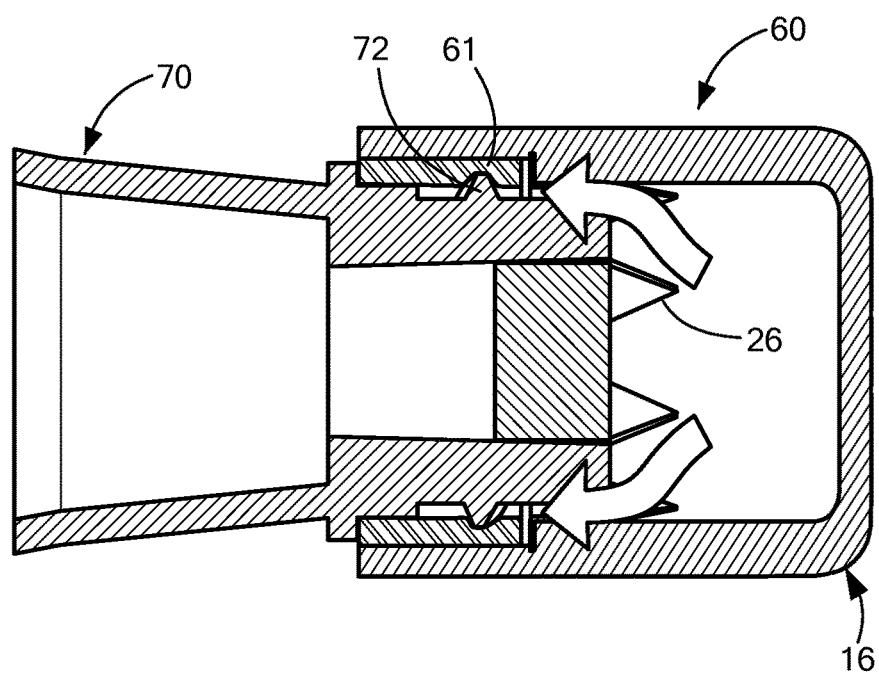

FIGS. 28-30 are side views of another cap 60 being installed on a needleless access site 70, and FIGS. 31-33 are sectional views of the same process. In FIGS. 28 and 31, the cap 60 and the NIS 70 are brought near each other; in FIGS. 29 and 32, the NIS 70 has started being inserted into the cap 60; and in FIGS. 30 and 33, the cap 60 is fully installed on the NIS 70. When the cap 60 is fully on the NIS 70, the seal 26 is broken and the antiseptic liquid disinfects the exposed surfaces of the NIS 70. FIGS. 31 and 32 show an absorbent pad 63 for holding the antiseptic liquid. In a preferred embodiment, the NIS 70 comes into contact with the absorbent pad 63 when fully inserted into the cap 60. The absorbent pad is not included in FIG. 33, so that the broken seal 26 can be more easily seen.

In this embodiment, a separate elastomeric or malleable material is included on the inner surface of the thread engagement region to form the complaint wall 61. This elastomeric or malleable material is a separate component which is inserted into the cap 60 as shown in FIGS. 31-33. The reservoir for holding the antiseptic liquid is formed with the main cap material. As can be seen in FIGS. 28-33, the threads 72 on the NIS 70 are accommodated by a compliant wall 61. In FIGS. 29 and 32, the threads 72 have begun to engage the compliant wall 61, but the NIS has not yet come into contact with the breakable seal 26. The compliant wall 61 may be configured to accept a number of different NIS sizes. In FIGS. 30 and 33, the threads 72 are more fully engaged by the compliant wall 61, and the NIS has broken through the seal 26. The white arrows shown in FIG. 33 show how the antiseptic liquid can flow from the distal portion around the edge of the NIS 70 so as to disinfect the sides as well as the face of the NIS.

Figure 34:
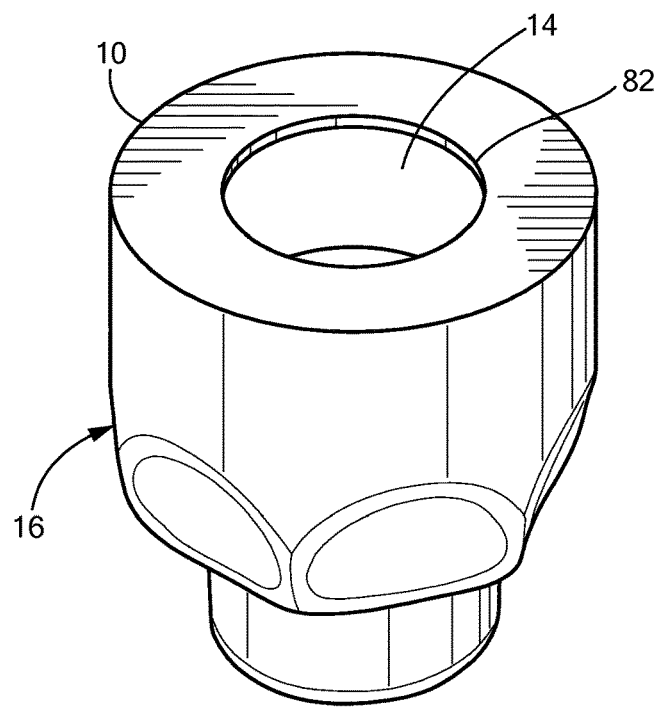
FIG. 34 is a perspective view of an alternative embodiment of a cap according to the present invention.
Figure 35:
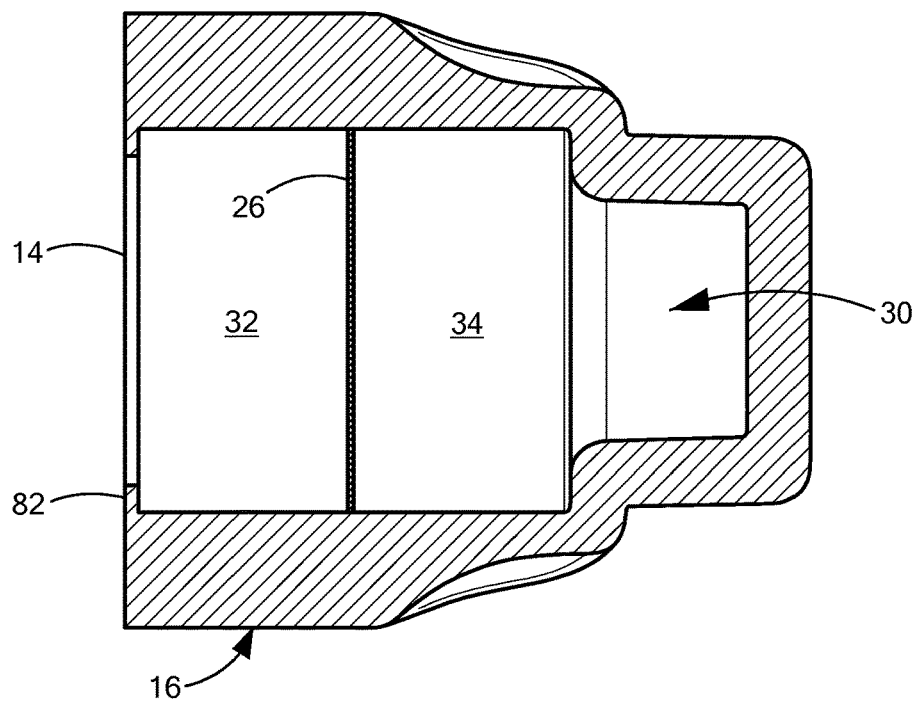
FIG. 35 is a sectional view of the FIG. 34 embodiment.

FIGS. 34 and 35 are perspective and sectional views of another cap embodiment. As in the prior embodiments, the cap includes a cap body 16, which defines a chamber 30, which is divided into a proximal portion 32 and a distal portion 34 by a breakable seal. Around the opening 14 at the proximal end 10 of the cap is a flexible skirt 82. This skirt 82 engages the outer diameter of the NIS, including any threads on the NIS, so as to hold the cap on the NIS.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A disinfecting cap for accepting a needleless injection site and applying an antiseptic agent to the needleless injection site, the cap comprising:
   a cap body defining a chamber having an opening at a proximal end for accepting the needleless injection site, the chamber having a proximal portion and a distal portion;
   an antiseptic agent disposed in the distal portion of the chamber; and
   a breakable seal located in the chamber between the proximal and distal portions so as to be spaced away from the opening, the breakable seal preventing evaporation of the antiseptic agent until the needleless injection site is accepted into the cap,
   wherein the cap body includes a compliant wall about the proximal portion,
   wherein the compliant wall deforms when the needleless injection site is inserted into the opening so that the compliant wall engages threading elements on the outer diameter of the needleless injection site to removably hold the cap on the needleless infection site.

2. The disinfecting cap of claim 1, wherein the breakable seal is oriented perpendicular to a longitudinal axis of the cap.

3. The disinfecting cap of claim 1, further including an absorbent material for holding the antiseptic agent, the absorbent material being disposed in the distal portion of the chamber.

4. The disinfecting cap of 1, wherein the compliant wall is made of a thermoplastic elastomer.

5. The disinfecting cap of 1, wherein the compliant wall is made of silicone.

6. A disinfecting cap for accepting a needleless injection site and applying an antiseptic agent to the needleless injection site, the cap comprising:
   a cap body defining a chamber having an opening at a proximal end for accepting the needleless injection site, the chamber having a proximal portion and a distal portion;
   an antiseptic agent disposed in the distal portion of the chamber; and
   a seal preventing evaporation of the antiseptic agent until the needleless injection site is accepted into the cap,
   wherein the cap body includes a compliant wall about the proximal portion, wherein the compliant wall deforms when the needleless injection site is inserted into the opening so that the compliant wall engages threading elements on the outer diameter of the needleless injection site to removably hold the cap on the needleless injection site.

7. The disinfecting cap of claim 6, further including an absorbent material for holding the antiseptic agent, the absorbent material being disposed in the distal portion of the chamber.

8. A system for disinfecting needleless injection sites, the system comprising:
   a plurality of caps for accepting a needleless injection site and applying an antiseptic agent to the needleless injection site, each cap including:
      a cap body defining a chamber having an opening at a proximal end for accepting the needleless injection site, the chamber having a proximal portion and a distal portion,
      an antiseptic agent disposed in the distal portion of the chamber, and
      a breakable seal located in the cavity between the proximal and distal portions so as to be spaced away from the opening, the breakable seal preventing evaporation of the antiseptic agent until the needleless injection site is accepted into the cap; and
   a carrier strip, wherein each of the plurality of caps is removably attached at its proximal end to the carrier strip, so that the opening in each of the caps is covered by the carrier strip,
   wherein the carrier strip includes projections, each projection shaped to engage the opening of the chamber so that the cap is removably attached to the projection.

* * * * *

UNITED STATES PATENT AND TRADEMARK OFFICE
CERTIFICATE OF CORRECTION

PATENT NO. : 10,166,339 B2
APPLICATION NO. : 14/947341
DATED : January 1, 2019
INVENTOR(S) : Solomon et al.

Page 1 of 1

It is certified that error appears in the above-identified patent and that said Letters Patent is hereby corrected as shown below:

In the Claims

Column 9, Line 34 reads, "... needleless infection ..." which should read, "... needleless injection ..."

Signed and Sealed this
Nineteenth Day of February, 2019

Andrei Iancu
*Director of the United States Patent and Trademark Office*